US011488700B2

(12) United States Patent
Monirabbasi et al.

(10) Patent No.: US 11,488,700 B2
(45) Date of Patent: Nov. 1, 2022

(54) MEDICAL DEVICE CONFIGURATION PROCEDURE GUIDANCE RESPONSIVE TO DETECTED GESTURES

(71) Applicant: MEDTRONIC MINIMED, INC., Northridge, CA (US)

(72) Inventors: Salman Monirabbasi, Playa Vista, CA (US); Di Wu, Glendale, CA (US); Neha J. Parikh, West Hills, CA (US); Yuxiang Zhong, Arcadia, CA (US); Maria Diana Miller, Santa Rosa Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 17/118,984

(22) Filed: Dec. 11, 2020

(65) Prior Publication Data

US 2021/0183489 A1  Jun. 17, 2021

Related U.S. Application Data

(60) Provisional application No. 62/947,997, filed on Dec. 13, 2019, provisional application No. 62/948,015, filed on Dec. 13, 2019.

(51) Int. Cl.
*G06F 3/048* (2013.01)
*G06F 3/01* (2006.01)
(Continued)

(52) U.S. Cl.
CPC .............. *G16H 20/17* (2018.01); *G06F 3/017* (2013.01); *G06F 3/048* (2013.01); *G16H 40/40* (2018.01)

(58) Field of Classification Search
CPC ........ G16H 20/17; G16H 40/40; G16H 40/63; G06F 3/048; G06F 3/017; G06F 1/1686; G06F 1/1694; G06F 1/3215; G06F 1/3231; G06F 3/0304; G06F 3/04895; Y02D 10/00
See application file for complete search history.

(56) References Cited

U.S. PATENT DOCUMENTS 4,562,751 A    1/1986  Nason et al.
4,685,903 A    8/1987  Cable et al.
(Continued)

*Primary Examiner* — Grant Sitta
(74) *Attorney, Agent, or Firm* — Weaver Austin Villeneuve & Sampson LLP

(57) ABSTRACT

Gesture-informed patient management systems and related medical devices and operating methods are provided. A method of assisting operation of a medical device using a sensing arrangement capable of detecting physical movement by a user involves detecting a configuration procedure performed by the user in response to output of the sensing arrangement indicative of one or more gestures with respect to the medical device by the user, determining a current state of the user within the configuration procedure based at least in part on the one or more gestures with respect to the medical device relative to a sequence of gestures corresponding to a defined sequence of tasks for the configuration procedure, and providing a graphical user interface display on a client device comprising guidance information influenced by the current state within the configuration procedure.

19 Claims, 9 Drawing Sheets

(51) Int. Cl.
*G16H 20/17* (2018.01)
*G16H 40/40* (2018.01)

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 * | 1/2013 | Rush ............... A61B 5/0002 604/503 |
| 8,352,011 B2 | 1/2013 | Van Antwerp et al. |
| 8,353,829 B2 | 1/2013 | Say et al. |
| 9,207,767 B2 * | 12/2015 | Bell ..................... G06F 3/017 |
| 9,517,109 B2 * | 12/2016 | Maeda ............. G02B 27/0103 |
| 11,037,070 B2 * | 6/2021 | Salganicoff ............ G06N 20/00 |
| 11,177,025 B2 * | 11/2021 | Bettencourt-Silva ..................... G16H 70/40 |
| 11,191,899 B2 * | 12/2021 | Roy ..................... G16H 20/60 |
| 11,197,949 B2 * | 12/2021 | Dang ................ A61M 5/14248 |
| 11,241,537 B2 * | 2/2022 | Jiang .................. A61M 5/1723 |
| 11,344,235 B2 * | 5/2022 | Nogueira .............. G16H 40/40 |
| 11,344,674 B2 * | 5/2022 | Palerm ................ A61M 5/1452 |
| 2007/0123819 A1 | 5/2007 | Mernoe et al. |
| 2010/0160861 A1 | 6/2010 | Causey, III et al. |
| 2012/0019369 A1 * | 1/2012 | Taskinen ............ G06K 7/10366 340/10.42 |
| 2012/0197196 A1 * | 8/2012 | Halbert ................... G16Z 99/00 604/151 |
| 2015/0126963 A1 * | 5/2015 | Despa .................... G16H 20/13 604/154 |
| 2016/0030683 A1 * | 2/2016 | Taylor .................. A61M 5/345 604/151 |
| 2016/0378939 A1 * | 12/2016 | Baumberger .......... G16H 20/40 705/2 |
| 2018/0353698 A1 * | 12/2018 | Saint ..................... A61M 5/347 |
| 2019/0117809 A1 * | 4/2019 | Katz ......................... G06T 7/50 |
| 2019/0380792 A1 * | 12/2019 | Poltaretskyi ........... A61B 90/06 |
| 2020/0054406 A1 * | 2/2020 | Hanuschik ............. A61B 34/30 |
| 2020/0111578 A1 * | 4/2020 | Koblick ................ G16H 20/10 |
| 2020/0135320 A1 | 4/2020 | Vleugels |
| 2020/0289373 A1 | 9/2020 | Vleugels |
| 2021/0178063 A1 * | 6/2021 | Parikh .................... G06V 40/23 |

\* cited by examiner

MEDICAL DEVICE CONFIGURATION PROCEDURE GUIDANCE RESPONSIVE TO DETECTED GESTURES

CROSS-REFERENCE TO RELATED APPLICATION

This application claims the benefit of U.S. Provisional Patent Application Ser. No. 62/947,997, which was filed on Dec. 13, 2019, and U.S. Provisional Patent Application Ser. No. 62/948,015, which was filed on Dec. 13, 2019, which are both incorporated by reference herein in their entirety.

TECHNICAL FIELD

The present technology is generally related to providing guidance pertaining to the control, operation, and adjustment of a medication delivery system in response to gestures detected by a gesture-based physical behavior detection system.

BACKGROUND

Medical therapy delivery systems, such as fluid infusion devices, are relatively well known in the medical arts for use in delivering or dispensing an agent, such as insulin or another prescribed medication, to a patient. A typical medication infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients. Configuring fluid infusion devices for operation often requires certain physical or mechanical tasks, such as, for example, filling a reservoir, rotating or replacing an infusion set or a glucose sensor, changing batteries, and/or the like. However, some users may find these procedures to be complex or burdensome (e.g., too many steps, too hard to remember, etc.), which can degrade the user experience or frustrate realization of the full benefits of infusion therapy.

BRIEF SUMMARY

The subject matter of this disclosure generally relates to gesture-informed patient management systems and related medical devices and operating methods for providing guidance related to operating or configuring a medical device or component in response to gestures detected using a gesture-based physical behavior detection system.

In one embodiment, a method of assisting operation of a medical device using a sensing arrangement capable of detecting physical movement by a user is provided. The method involves detecting, by a control system associated with the medical device, a configuration procedure performed by the user in response to output of the sensing arrangement indicative of one or more gestures with respect to the medical device by the user, determining, by the control system, a current state of the user within the configuration procedure based at least in part on the one or more gestures with respect to the medical device relative to a sequence of gestures corresponding to a defined sequence of tasks for the configuration procedure, and providing, by the control system, a graphical user interface display on a client device. The graphical user interface display includes guidance information influenced by the current state within the configuration procedure.

In another embodiment, at least one non-transitory computer readable medium having stored thereon program code instructions is provided. The program code instructions are configurable to cause at least one processor to detect a configuration procedure performed by a user with respect to a medical device in response to output of a sensing arrangement indicative of one or more gestures with respect to the medical device by the user where the sensing arrangement is capable of detecting physical movement by the user, determine a current state of the user within the configuration procedure based at least in part on the one or more gestures with respect to the medical device relative to a sequence of gestures corresponding to a defined sequence of tasks for the configuration procedure, and provide a graphical user interface display comprising guidance information influenced by the current state within the configuration procedure.

In yet another embodiment, a system is provided that includes a medical device that regulates delivery of fluid to a patient, a gesture detection system configured to generate gesture data for the patient, and configured to communicate the gesture data, and at least one controller that controls operation of the medical device. The at least one controller is configured to detect a configuration procedure performed by the patient in response to the gesture data indicative of one or more procedural gestures with respect to the medical device by the patient, determine a current state of the patient within the configuration procedure based at least in part on the one or more procedural gestures with respect to the medical device relative to a sequence of gestures corresponding to a defined sequence of tasks for the configuration procedure, and provide a graphical user interface display comprising guidance information influenced by the current state within the configuration procedure.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
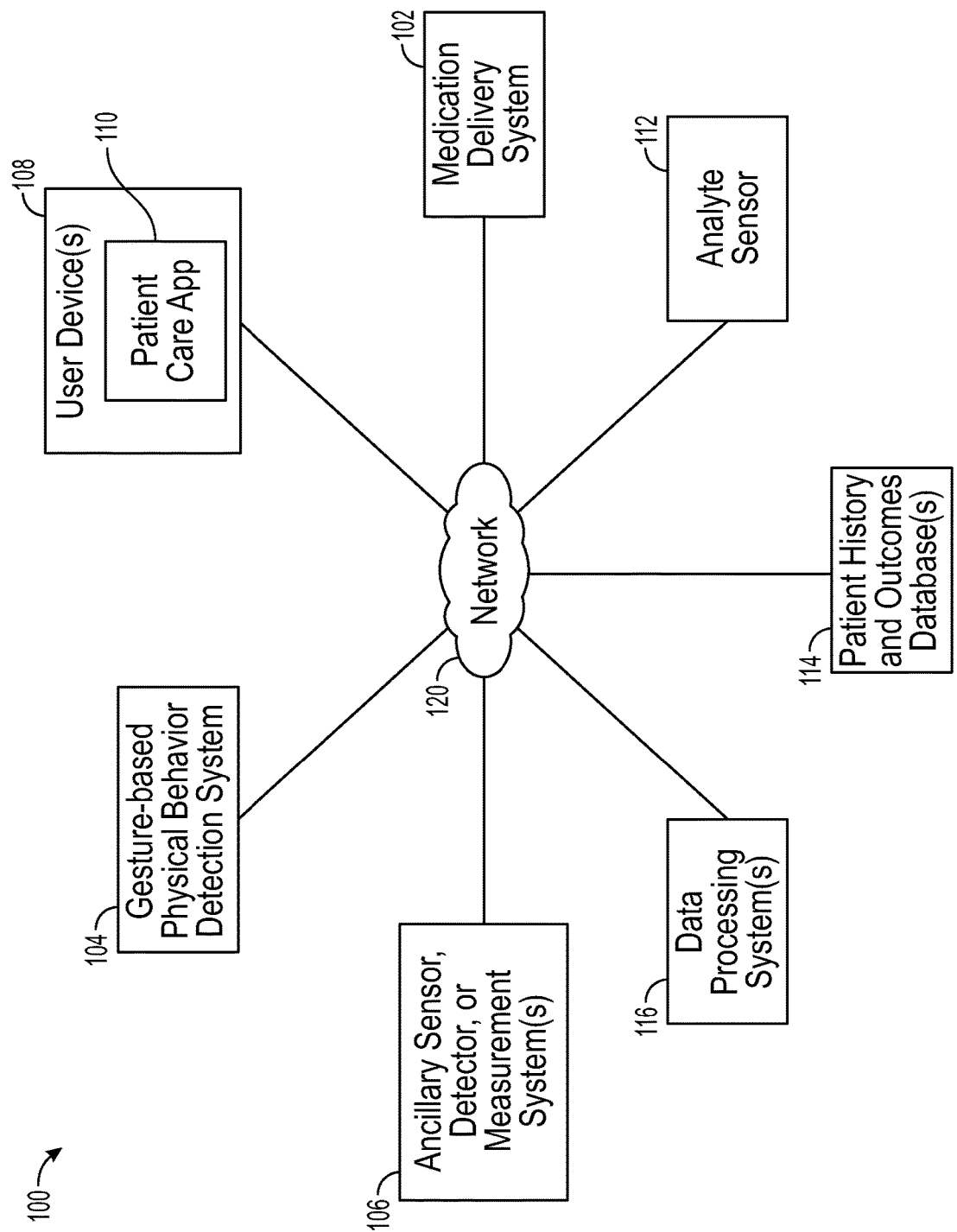
FIG. 1 is a simplified block diagram representation of an exemplary embodiment of a system that includes a medication delivery system that responds to changes in patient activity as indicated by the output of a gesture-based physical behavior detection system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more exemplary embodiments, the subject matter described herein is implemented in connection with a portable electronic medical device. Although many different applications are possible, for purposes of explanation, the following description may focus on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Program code instructions may be configurable to be executed by one or more processors, such as one or more digital signal processors (DSPs), general purpose microprocessors, controllers, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

FIG. 1 is a simplified block diagram representation of an exemplary embodiment of a system 100 that regulates operation of a medication delivery system 102 or other medical device to thereby regulate a physiological condition of a patient user in response to events or other activities (e.g., eating, sleeping, exercise, and/or working, and/or the like) detected based on physical movements by the patient. In certain embodiments, the medication delivery system 102 responds to the patient's behavior as indicated by the output of a gesture-based physical behavior detection system 104 and/or the output of at least one ancillary sensor, detector, or measurement system 106 (hereinafter referred to as ancillary system(s) 106). Certain embodiments of the system 100 include, without limitation: the medication delivery system 102 (or device) that regulates delivery of medication to a patient user; at least one gesture-based physical behavior detection system 104 that monitors user behavior and/or status to obtain gesture data that indicates user activity events or behavior; at least one ancillary system 106; at least one user device 108 that includes or cooperates with a suitably written and configured patient care application 110; an analyte sensor 112 to measure a physiological characteristic of the user, such that sensor data obtained from the analyte sensor 112 can be used to control, regulate, or otherwise influence the operation of the medication delivery system 102; and at least one patient history and outcomes database 114. In accordance with certain cloud-implemented embodiments, the system includes at least one data processing system 116, which may be in communication with any or all of the other components of the system 100. Other configurations and topologies for the system 100 are also contemplated here, such as a system that includes additional intermediary, interface, or data repeating devices in the data path between a sending device and a receiving device.

As described in greater detail below in the context of FIG. 1, in one or more exemplary embodiments, the system 100 is configured to support a procedural gesture guidance process for providing guidance or instructions (e.g., via patient care application 110 at a user device 108) with respect to configuration procedure being performed with respect to a medical device or component of the medical delivery system 102, the analyte sensor 112, or an ancillary system 106 responsive to procedural gestures detected by the gesture-based physical behavior detection system 104. For example, the particular medical device or component associated with the medical delivery system 102, the analyte sensor 112, or the ancillary system 106 may have one or more configuration procedures for operating the respective medical device or component. In this regard, a medical device configuration procedure generally involves a sequence or combination of one or more physical or mechanical tasks for installing, setting up, programming, operating or otherwise configuring the medical device for subsequent operation, such as, for example, changing, rotating or replacing an infusion set associated with the medical delivery system 102; changing, replacing or refilling a reservoir of the medical delivery system 102; priming a reservoir of the medical delivery system 102; replacing an insulin cartridge of an infusion device, injection device, or other medical device of the medical delivery system 102; refilling an insulin cartridge of an infusion device, injection device, or other medical device of the medical delivery system 102; shaking or agitating an infusion device, injection device, or other medical device of the medical delivery system 102 to mix the contents of an insulin cartridge or fluid reservoir; charging, changing or replacing batteries of an infusion device, injection device, smart insulin pen cap, or other medical device of the medical delivery system 102; injecting or otherwise delivering insulin or another fluid or medicament using an injection device or other medical device of the medical delivery system 102; replacing needle of an infusion device, injection device, or other medical device of the medical delivery system 102; cleaning an infusion device, injection device, or other medical device of the medical delivery system 102; changing, rotating or replacing the analyte sensor 112; charging, changing or replacing batteries of the analyte sensor 112; taking glucose reference measurements via the analyte sensor 112 or another ancillary system 106 (e.g., a blood glucose fingerstick reference measurement via a blood glucose meter); turning off, disabling or otherwise addressing alarms, alerts or other user notifications generated by an infusion device, injection device, or other medical device of the medical delivery system 102; and/or the like.

Due to the number of potential different configuration procedures required to support proper operation of the system as well as the potential complexities of the configuration procedures, the exact tasks (and sequence thereof) can be difficult to remember or follow for some individuals. Accordingly, the gesture-based detection system 104 is configured to detect when a patient or other user is performing one or more procedural gestures with respect to a device or component 102, 106, 112 of the system 100 and thereby detect where the patient or user is within a particular medical device configuration procedure with respect to that particular device or component 102, 106, 112. Based on the determination of the current state of the user within the identified configuration, the patient care application 110 may be utilized to provide appropriate guidance or training materials to support completion of the defined sequence of physical or mechanical tasks for the configuration procedure accurately and expeditiously. For example, one or more graphical user interface (GUI) displays may be provided by the patient care application 110 on the user device 108 to provide step-by-step guidance for completing the configuration procedure from the current state within the configuration procedure. Additionally, or alternatively, the patient care application 110 may provide auditory output of the step-by-step guidance to one or more speakers of user device 108. In some examples, one or more GUIs may be displayed on a display of the gesture-based physical behavior detection system 104 (e.g., on a display of a smart watch).

For example, when the detected gesture data identified by the gesture-based physical detection system 104 indicates the patient is attempting to replace or change the analyte sensor 112, the patient care application 110 may automatically generate GUI displays or other user notifications to provide step-by-step guidance for replacing the analyte sensor 112. As another example, when the detected gesture data identified by the gesture-based physical detection system 104 indicates the patient is attempting to rotate, replace or change an infusion set associated with the medical delivery system 102, the patient care application 110 may automatically generate GUI displays or other user notifications to provide step-by-step guidance for rotating or replacing the infusion set. It should be appreciated that the subject matter is not limited to any particular type or manner of providing guidance for completing a configuration procedure, nor is the subject matter limited to any particular type of configuration procedure. In this regard, various embodiments may incorporate or otherwise support chatbot functionality or other features in connection with the guidance information to allow a patient or other user to obtain answers to frequently asked questions, interface with training materials, or otherwise receive support that improves the user experience.

Referring again to FIG. 1, at least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

The system 100 can support any type of medication delivery system 102 that is compatible with the features and functionality described here. For example, the medication delivery system 102 may be realized as a user-activated or user-actuated fluid delivery device, such as a manual syringe, an injection pen, or the like. As another example, the medication delivery system 102 may be implemented as an electronic device that is operated to regulate the delivery of medication fluid to the user. In certain embodiments, however, the medication delivery system 102 includes or is realized as an insulin infusion device, e.g., a portable patient-worn or patient-carried insulin pump, a smart insulin pen, or the like. In such embodiments, the analyte sensor 112 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Figure 2:
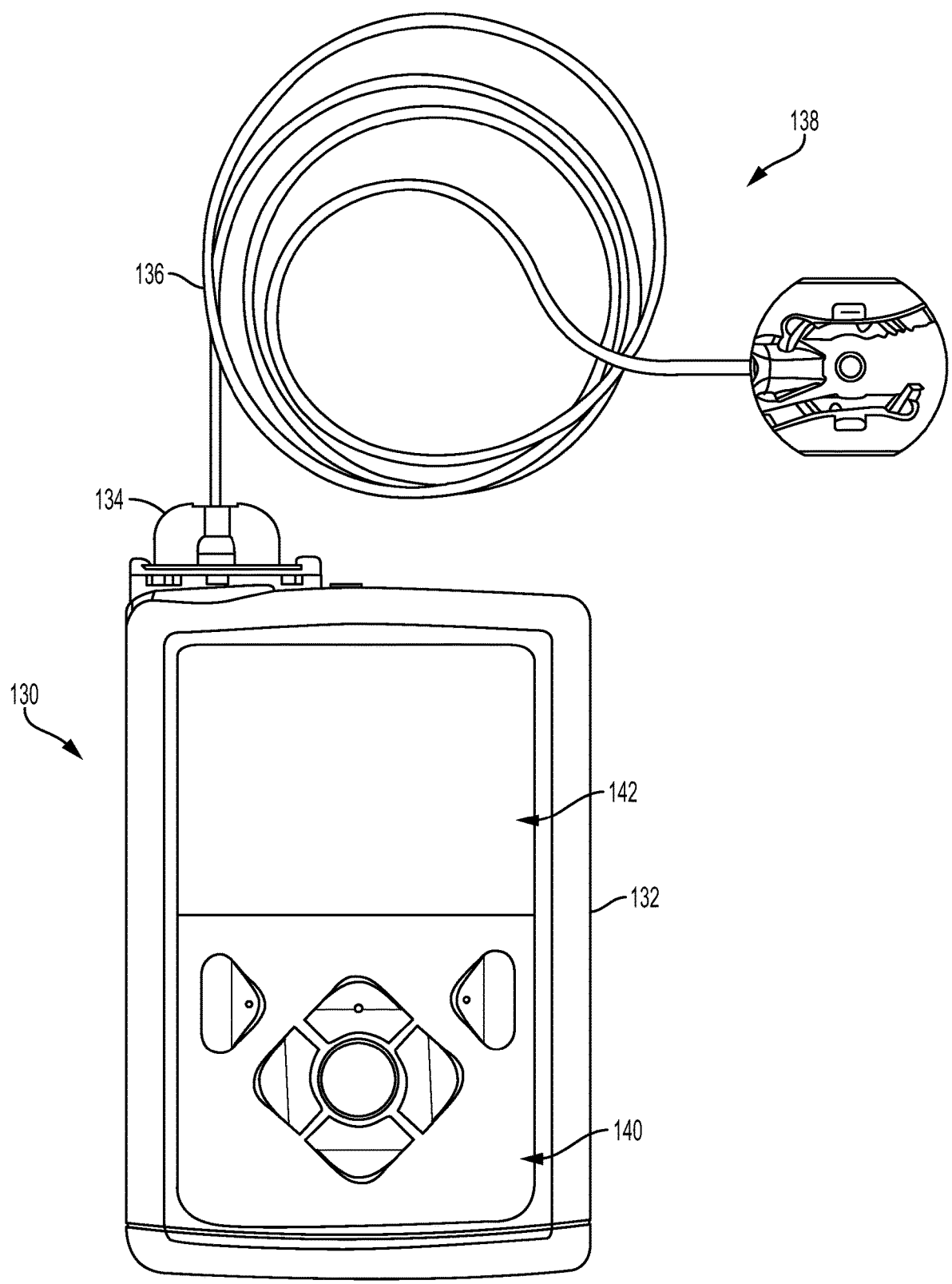
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3:
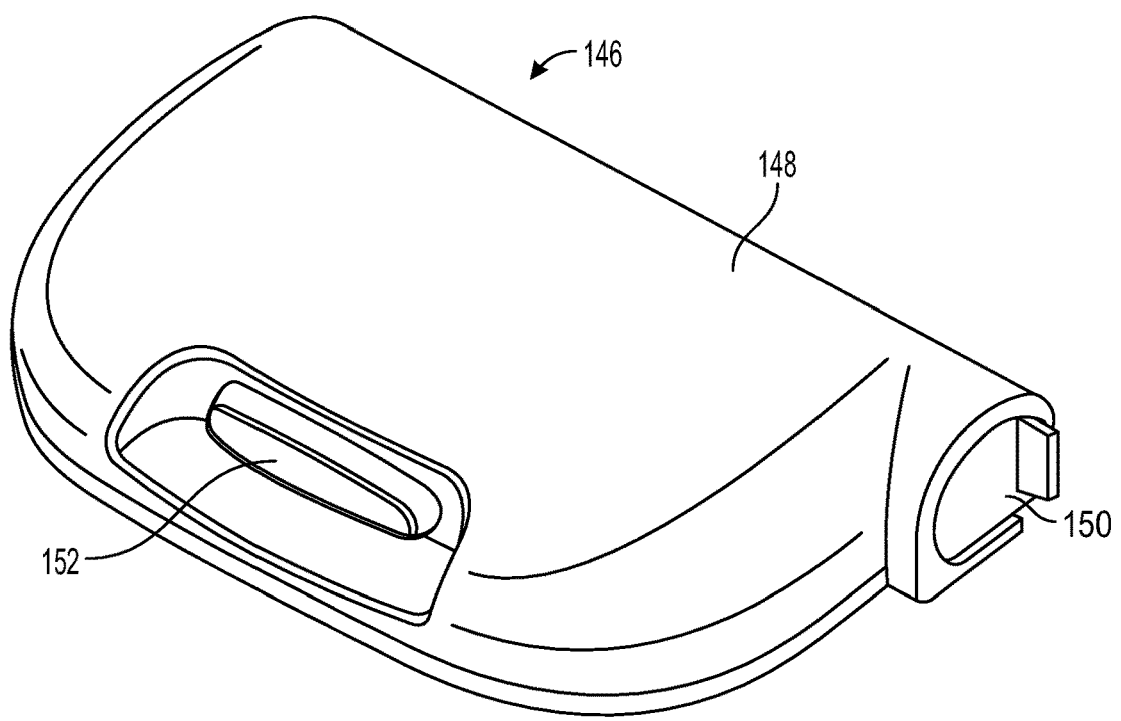
FIG. 3 is a top perspective view of an embodiment of an insulin infusion device implemented as a patch pump device that is suitable for use as the medication delivery system shown in FIG. 1.

FIG. 3 is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3). In such an implementation, the glucose sensor may take the place of the separate analyte sensor 112 shown in FIG. 1. The insulin infusion device 146 includes a housing 148 that serves as a shell for a variety of internal components. FIG. 3 shows the insulin infusion device 146 with a removable fluid cartridge 150 installed and secured therein. The housing 148 is suitably configured to receive, secure, and release the removable fluid cartridge 150. The insulin infusion device 146 includes at least one user interface feature, which can be actuated by the patient as needed. The illustrated embodiment of the fluid infusion device 146 includes a button 152 that is physically actuated. The button 152 can be a multipurpose user interface if so desired to make it easier for the user to operate the fluid infusion device 146. In this regard, the button 152 can be used in connection with one or more of the following functions, without limitation: waking up the processor and/or electronics of the fluid infusion device 146; triggering an insertion mechanism to insert a fluid delivery cannula and/or an analyte sensor into the subcutaneous space or similar region of the user; configuring one or more settings of the fluid infusion device 146; initiating delivery of medication fluid from the fluid cartridge 150; initiating a fluid priming operation; disabling alerts or alarms generated by the fluid infusion device 146; and the like. In lieu of the button 152, the insulin infusion device 146 can employ a slider mechanism, a pin, a lever, a switch, a touch-sensitive element, or the like. In certain embodiments, the insulin infusion device 146 may be configured and controlled to support other features and interactive functions described in more detail below.

Generally, a fluid infusion device (such as an insulin infusion device) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 4:
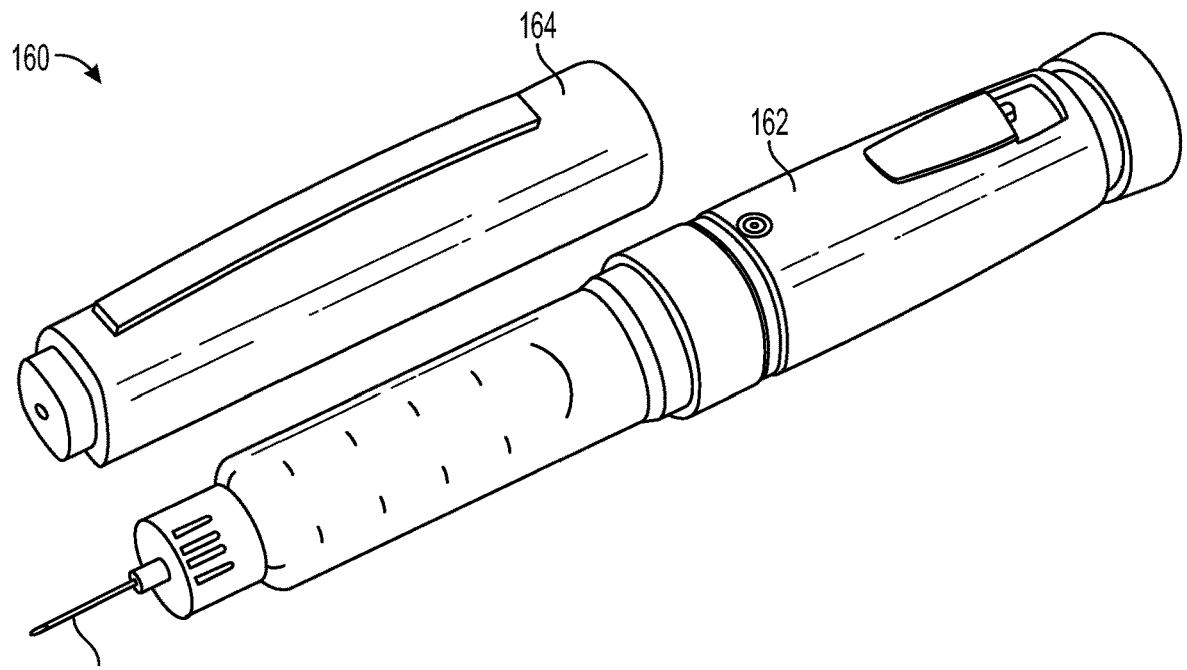
FIG. 4 is a perspective view of an exemplary embodiment of a smart insulin pen that is suitable for use as the medication delivery system shown in FIG. 1.

FIG. 4 is a perspective view of an exemplary embodiment of a smart insulin pen 160 suitable for use as the medication delivery system shown in FIG. 1. The pen 160 includes an injector body 162 and a cap 164. FIG. 4 shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 5:
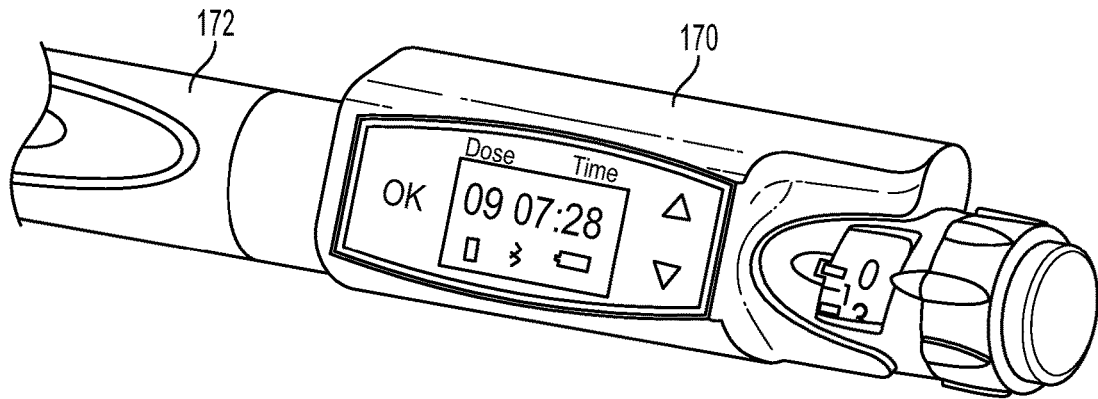
FIG. 5 is a perspective view of an exemplary embodiment of a smart pen accessory that is suitable for use with the medication delivery system shown in FIG. 1.

FIG. 5 is a perspective view of an exemplary embodiment of a smart pen accessory 170 that is suitable for use with the medication delivery system 102 shown in FIG. 1. In particular, the smart pen accessory 170 cooperates with a "non-smart" insulin pen that lacks the intelligence and functionality of a smart insulin pen (as described above). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described above in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

Referring again to FIG. 1, the analyte sensor 112 may communicate sensor data to the medication delivery system 102 for use in regulating or controlling operation of the medication delivery system 102. Alternatively, or additionally, the analyte sensor 112 may communicate sensor data to one or more other components in the system 100, such as, without limitation: a user device 108 (for use with the patient care application 110); a data processing system 116; and/or a patient history and outcomes database 114.

The system 100 can support any number of user devices 108 linked to the particular user or patient. In this regard, a user device 108 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. For the example described here, the medication delivery system 102 and the at least one user device 108 are owned by, operated by, or otherwise linked to a user/patient. Any given user device 108 can host, run, or otherwise execute the patient care application 110. In certain embodiments, for example, the user device 108 is implemented as a smartphone with the patient care application 110 installed thereon. In accordance with another example, the patient care application 110 is implemented in the form of a web site or webpage, e.g., a web site of a healthcare provider, a web site of the manufacturer, supplier, or retailer of the medication delivery system 102, or a website of the manufacturer, supplier, or retailer of the analyte sensor 112. In accordance with another example, the medication delivery system 102 executes the patient care application 110 as a native function. In certain embodiments, at least some of the features or output of the gesture-based physical behavior detection system 104 and/or the ancillary system(s) 106 can be used to influence features, functions, and/or therapy-related operations of the medication delivery system 102.

As described in more detail below, the gesture-based physical behavior detection system 104 includes one or more sensors, detectors, measurement devices, and/or readers to automatically detect certain user gestures that correlate to user activities or events (e.g., work-related physical activity, commuting, eating at common meal times, sleeping, exercising, or watching television). The gesture-based physical behavior detection system 104 may communicate gesture data to the medication delivery system 102, the user device 108, and/or the data processing system 116 for processing in an appropriate manner for use in regulating or controlling certain functions of the medication delivery system 102. For example, the gesture data may be communicated to a user device 108, such that the user device 108 can process the gesture data and inform the user or the medication delivery system 102 as needed (e.g., remotely regulate or control certain functions of the medication delivery system 102). As another example, the gesture-based physical behavior detection system 104 may communicate the gesture data to one or more cloud computing systems or servers (such as a remote data processing system 116) for appropriate processing and handling in the manner described herein.

Similarly, an ancillary system 106 may include one or more sensors, detectors, measurement devices, and/or readers that obtain ancillary user status data that correlates to events or activity by a user. In certain embodiments, an ancillary system 106 may include, cooperate with, or be realized as any of the following, without limitation: a heartrate monitor linked to the user; a blood pressure monitor linked to the user; a respiratory rate monitor linked to the user; a vital signs monitor linked to the user; a microphone; a thermometer (for the user's body temperature and/or the environmental temperature); a sweat detector linked to the user; an activity tracker linked to the user; a global positioning system (GPS); a clock, calendar, or appointment application linked to the user; a pedometer linked to the user; or the like. An ancillary system 106 may be configured and operated to communicate its output (user status data) to one or more components of the system 100 for analysis, processing, and handling in the manner described herein. In certain embodiments, user status data obtained from one or more ancillary systems 106 supplements the gesture data obtained from the gesture-based physical behavior detection system 104, such that user habits, physical behavior, and activity events are accurately and reliably detected.

In certain embodiments, the gesture-based physical behavior detection system 104 and the medication delivery system 102 are implemented as physically distinct and separate components, as depicted in FIG. 1. In such embodiments, the gesture-based physical behavior detection system 104 is external to the medication delivery system 102 and is realized as an ancillary component, relative to the medication delivery system 102. In accordance with alternative embodiments, however, the medication delivery system 102 and the gesture-based physical behavior detection system 104 can be combined into a single hardware component or provided as a set of attached hardware devices. For example, the medication delivery system 102 may include the gesture-based physical behavior detection system 104 or integrate the functionality of the detection system 104. Similarly, the analyte sensor 112 can be incorporated with the medication delivery system 102 or the gesture-based physical behavior detection system 104. These and other arrangements, deployments, and topologies of the system 100 are contemplated by this disclosure.

The at least one patient history and outcomes database 114 includes historical data related to the user's physical condition, physiological response to the medication regulated by the medication delivery system 102, activity patterns or related information, eating patterns and habits, work habits, and the like. In accordance with embodiments where the medication delivery system 102 is an insulin infusion device and the analyte sensor 112 is a glucose meter, sensor, or monitor, the database 114 can maintain any of the following, without limitation: historical glucose data and corresponding date/time stamp information; insulin delivery and dosage information; user-entered stress markers or indicators; gesture data (provided by the gesture-based physical behavior detection system 104) and corresponding date/time stamp information; ancillary user status data (provided by one or more ancillary systems 106) and corresponding date/time stamp data; diet or food intake history for the user; and any other information that may be generated by or used by the system 100 for purposes of controlling the operation of the medication delivery system 102. In certain embodiments, the at least one patient history and outcomes database 114 can receive and maintain training data that is utilized to train, configure, and initialize the system 100 based on historical user behavior, physiological state, operation of the medication delivery system 102, and user-identified activity events.

A patient history and outcomes database 114 may reside at a user device 108, at the medication delivery system 102, at a data processing system 116, or at any network-accessible location (e.g., a cloud-based database or server system). In certain embodiments, a patient history and outcomes database 114 may be included with the patient care application 110. The patient history and outcomes database 114 enables the system 100 to generate recommendations, warnings, and guidance for the user and/or to regulate the manner in which the medication delivery system 102 functions to administer therapy to the user, based on detected user activity.

Figure 6:
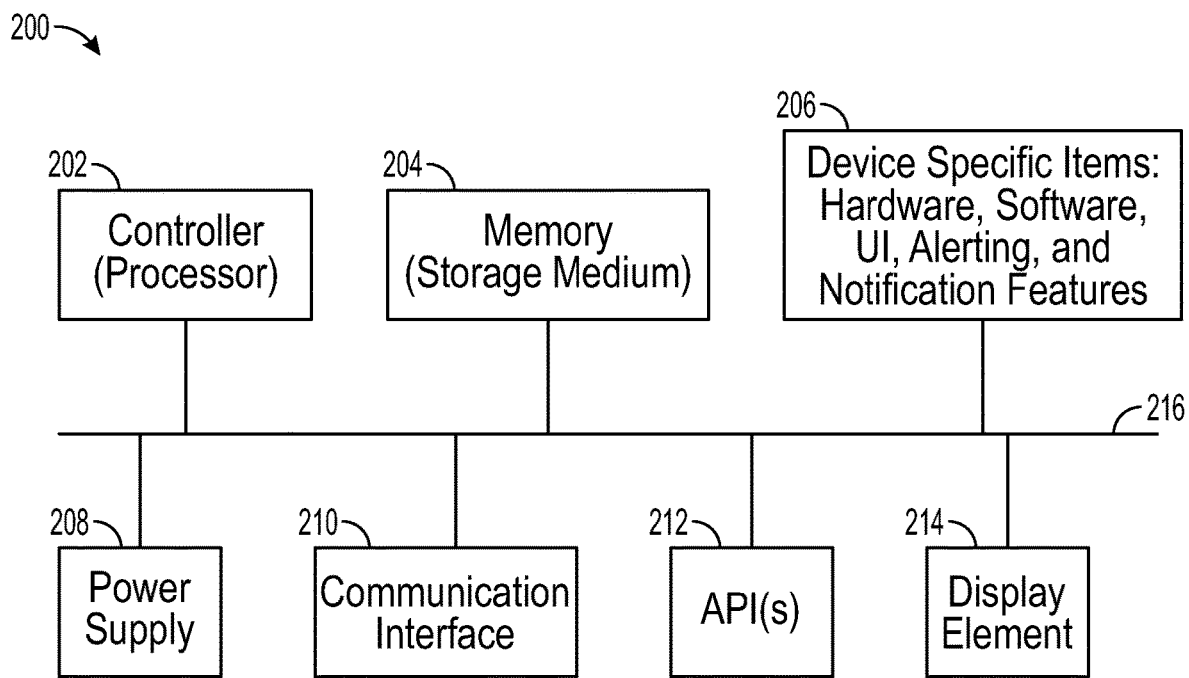
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 200 that is suitable for deployment in the system 100 shown in FIG. 1.

The illustrated embodiment of the device 200 is intended to be a high-level and generic representation of one suitable platform. In this regard, any computer-based or processor-based component of the system 100 can utilize the architecture of the device 200. The illustrated embodiment of the device 200 generally includes, without limitation: at least one controller (or processor) 202; a suitable amount of memory 204 that is associated with the at least one controller 202; device-specific items 206 (including, without limitation: hardware, software, firmware, user interface (UI), alerting, and notification features); a power supply 208 such as a disposable or rechargeable battery; a communication device 210; at least one application programming interface (API) 212; and a display element 214. Of course, an implementation of the device 200 may include additional elements, components, modules, and functionality configured to support various features that are unrelated to the primary subject matter described here. For example, the device 200 may include certain features and elements to support conventional functions that might be related to the particular implementation and deployment of the device 200. In practice, the elements of the device 200 may be coupled together via at least one bus or any suitable interconnection architecture 216.

The at least one controller 202 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 204 can be coupled to the at least one controller 202 such that the at least one controller 202 can read information from, and write information to, the memory 204. In the alternative, the memory 204 may be integral to the at least one controller 202. As an example, the at least one controller 202 and the memory 204 may reside in an ASIC. At least a portion of the memory 204 can be realized as a computer storage medium that is operatively associated with the at least one controller 202, e.g., a tangible, non-transitory computer-readable medium having computer-executable instructions stored thereon. The computer-executable instructions are configurable to be executed by the at least one controller 202 to cause the at least one controller 202 to perform certain tasks, operations, functions, and processes that are specific to the particular embodiment. In this regard, the memory 204 may represent one suitable implementation of such computer-readable media. Alternatively, or additionally, the device 200 could receive and cooperate with computer-readable media (not separately shown) that is realized as a portable or mobile component or platform, e.g., a portable hard drive, a USB flash drive, an optical disc, or the like.

The device-specific items 206 may vary from one embodiment of the device 200 to another. For example, the device-specific items 206 will support: sensor device operations when the device 200 is realized as a sensor device; smartphone features and functionality when the device 200 is realized as a smartphone; activity tracker features and functionality when the device 200 is realized as an activity tracker; smart watch features and functionality when the device 200 is realized as a smart watch; medical device features and functionality when the device is realized as a medical device; etc. In practice, certain portions or aspects of the device-specific items 206 may be implemented in one or more of the other blocks depicted in FIG. 6.

If present, the UI of the device 200 may include or cooperate with various features to allow a user to interact with the device 200. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The UI may include one or more graphical user interface (GUI) control elements that enable a user to manipulate or otherwise interact with an application via the display element 214. The display element 214 and/or the device-specific items 206 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication device 210 facilitates data communication between the device 200 and other components as needed during the operation of the device 200. In the context of this description, the communication device 210 can be employed to transmit or stream device-related control data, patient-related user status (e.g., gesture data or status data), device-related status or operational data, sensor data, calibration data, and the like. It should be appreciated that the particular configuration and functionality of the communication device 210 can vary depending on the hardware platform and specific implementation of the device 200. In practice, an embodiment of the device 200 may support wireless data communication and/or wired data communication, using various data communication protocols. For example, the communication device 210 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication device 210 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 212 supports communication and interactions between software applications and logical components that are associated with operation of the device 200. For example, one or more APIs 212 may be configured to facilitate compatible communication and cooperation with the patient care application 110, and to facilitate receipt and processing of data from sources external to the device 200 (e.g., databases or remote devices and systems).

The display element 214 is suitably configured to enable the device 200 to render and display various screens, recommendation messages, alerts, alarms, notifications, GUIs, GUI control elements, drop down menus, auto-fill fields, text entry fields, message fields, or the like. Of course, the display element 214 may also be utilized for the display of other information during the operation of the device 200, as is well understood. Notably, the specific configuration, operating characteristics, size, resolution, and functionality of the display element 214 can vary depending upon the implementation of the device 200.

Figure 7:
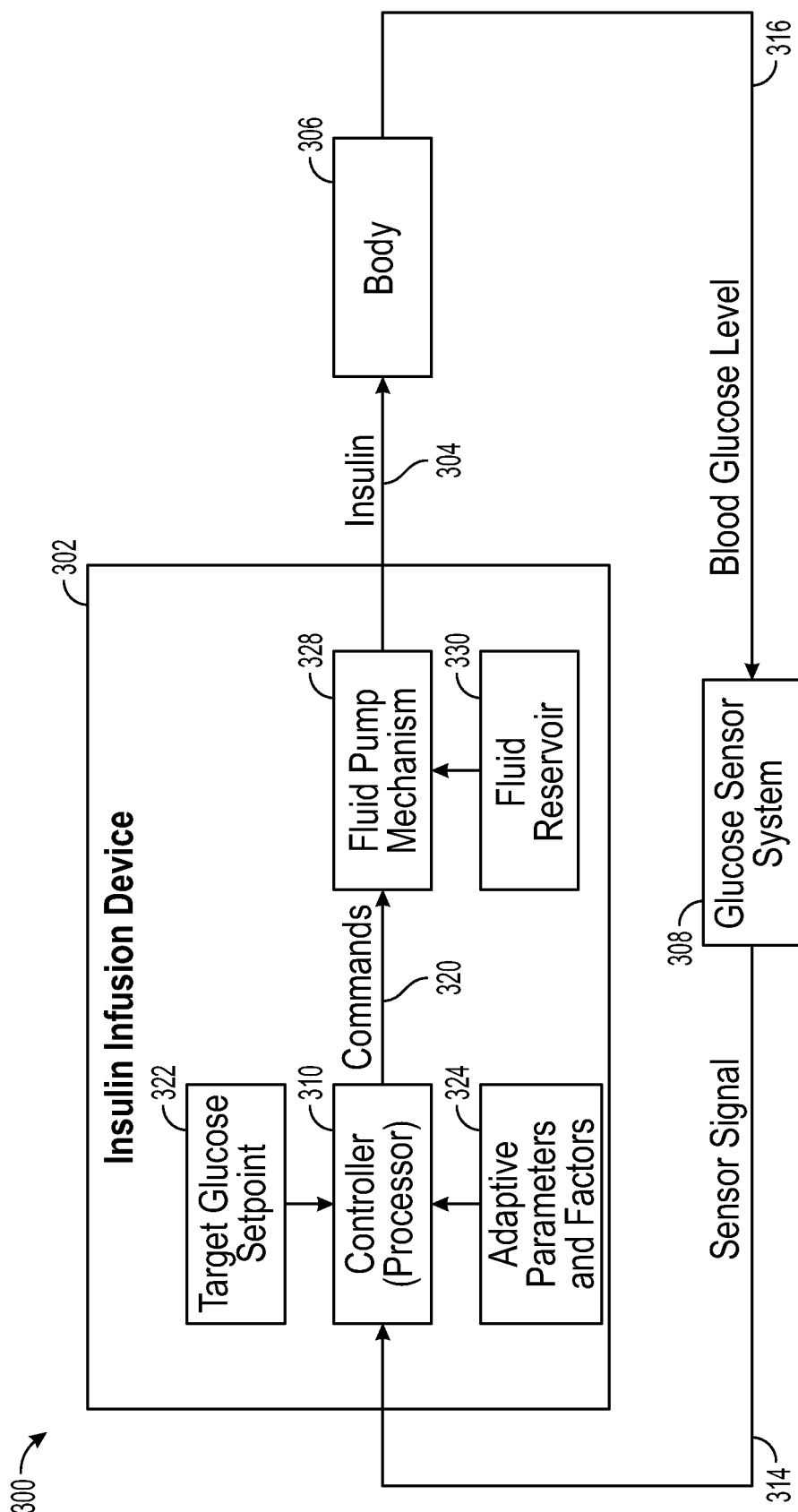
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 300 arranged in accordance with certain embodiments. The system 300 depicted in FIG. 7 functions to regulate the rate of fluid infusion into a body of a user based on feedback from an analyte concentration measurement taken from the body. In particular embodiments, the system 300 is implemented as an automated control system for regulating the rate of insulin infusion into the body of a user based on a glucose concentration measurement taken from the body. The system 300 is designed to model the physiological response of the user to control an insulin infusion device 302 in an appropriate manner to release insulin 304 into the body 306 of the user in a similar concentration profile as would be created by fully functioning human β-cells when responding to changes in blood glucose concentrations in the body. Thus, the system 300 simulates the body's natural insulin response to blood glucose levels and not only makes efficient use of insulin, but also accounts for other bodily functions as well since insulin has both metabolic and mitogenic effects.

Certain embodiments of the system 300 include, without limitation: the insulin infusion device 302; a glucose sensor system 308 (e.g., the analyte sensor 112 shown in FIG. 1); and at least one controller 310, which may be incorporated in the insulin infusion device 302 as shown in FIG. 7. The glucose sensor system 308 generates a sensor signal 314 representative of blood glucose levels 316 in the body 306, and provides the sensor signal 314 to the at least one controller 310. The at least one controller 310 receives the sensor signal 314 and generates commands 320 that regulate the timing and dosage of insulin 304 delivered by the insulin infusion device 302. The commands 320 are generated in response to various factors, variables, settings, and control algorithms utilized by the insulin infusion device 302. For example, the commands 320 (and, therefore, the delivery of insulin 304) can be influenced by a target glucose setpoint value 322 that is maintained and regulated by the insulin infusion device 302. Moreover, the commands 320 (and, therefore, the delivery of insulin 304) can be influenced by any number of adaptive parameters and factors 324. The adaptive parameters and factors 324 may be associated with or used by: a therapy control algorithm of the insulin infusion device 302; a digital twin model of the patient, which can be used to recommend manual insulin dosages; a meal prediction algorithm; a user glucose prediction algorithm; or the like.

Generally, the glucose sensor system 308 includes a continuous glucose sensor, sensor electrical components to provide power to the sensor and generate the sensor signal 314, a sensor communication system to carry the sensor signal 314 to the at least one controller 310, and a sensor system housing for the electrical components and the sensor communication system. As mentioned above with reference to FIG. 6, the glucose sensor system 308 may be implemented as a computer-based or processor-based component having the described configuration and features.

Typically, the at least one controller 310 includes controller electrical components and software to generate commands for the insulin infusion device 302 based on the sensor signal 314, the target glucose setpoint value 322, the adaptive parameters and factors 324, and other user-specific parameters, settings, and factors. The at least one controller 310 may include a controller communication system to receive the sensor signal 314 and issue the commands 320.

Generally, the insulin infusion device 302 includes a fluid pump mechanism 328, a fluid reservoir 330 for the medication (e.g., insulin), and an infusion tube to infuse the insulin 304 into the body 306. In certain embodiments, the insulin infusion device 302 includes an infusion communication system to handle the commands 320 from the at least one controller 310, electrical components and programmed logic to activate the fluid pump mechanism 328 motor according to the commands 320, and a housing to hold the components of the insulin infusion device 302. Accordingly, the fluid pump mechanism 328 receives the commands 320 and delivers the insulin 304 from the fluid reservoir 330 to the body 306 in accordance with the commands 320. It should be appreciated that an embodiment of the insulin infusion device 302 can include additional elements, components, and features that may provide conventional functionality that need not be described herein. Moreover, an embodiment of the insulin infusion device 302 can include alternative elements, components, and features if so desired, as long as the intended and described functionality remains in place. In this regard, as mentioned above with reference to FIG. 6, the insulin infusion device 302 may be implemented as a computer-based or processor-based components having the described configuration and features, including the display element 214 or other device-specific items 206 as described above.

The controller 310 is configured and programmed to regulate the operation of the fluid pump mechanism 328 and other functions of the insulin infusion device 302. The controller 310 controls the fluid pump mechanism 328 to deliver the fluid medication (e.g., insulin) from the fluid reservoir 330 to the body 306. As mentioned above, the controller 310 can be housed in the infusion device housing, wherein the infusion communication system is an electrical trace or a wire that carries the commands 320 from the controller 310 to the fluid pump mechanism 328. In alternative embodiments, the controller 310 can be housed in the sensor system housing, wherein the sensor communication system is an electrical trace or a wire that carries the sensor signal 314 from the sensor electrical components to the at least one controller 310. In accordance with some embodiments, the at least one controller 310 has its own housing or is included in a supplemental or ancillary device. In other embodiments, the at least one controller 310, the insulin infusion device 302, and the glucose sensor system 308 are all located within one common housing.

Referring again to FIG. 1, the gesture-based physical behavior detection system 104 employs at least one sensor to obtain corresponding user-specific sensor data. The obtained user-specific sensor data is processed or analyzed by the gesture-based physical behavior detection system 104 and/or by another suitably configured device or component of the system 100 to determine whether the user's current behavior reflects a significant or measurable change in activity. The obtained user-specific sensor data may also be processed or analyzed to obtain certain activity-related parameters, characteristics, and/or metadata for the user. For example, the obtained user-specific sensor data may identify, include, or indicate any or all of the following, without limitation: timestamp data corresponding to the occurrence of detected events; a type, category, or classification of the detected physical behavior or activity; location data; user posture or position information; etc.

The gesture-based physical behavior detection system 104 may include, cooperate with, or be realized as a motion-based physical behavior detection system, an activity-based physical behavior detection system, an image or video based activity detection system, or the like. In certain embodiments, the detection system 104 may be realized as a unitary "self-contained" wearable system that communicates with one or more other components of the system 100. For example, the detection system 104 can be implemented with at least one wearable device such as an activity monitor device, a smart watch device, a smart bracelet or wristband device, or the like. In some embodiments, the detection system 104 may be realized as at least one portable or wearable device that includes or communicates with one or more external or ancillary sensor devices, units, or components. For example, the detection system 104 can be implemented with a wearable or portable smart device that is linked with one or more external sensors worn or carried by the user. These and other possible deployments of the detection system 104 are contemplated by this disclosure. In this regard, United States patent publication number US 2020/0135320 and United States patent publication number US 2020/0289373 disclose gesture-based physical behavior detection systems that are suitable for use as the detection system 104; the entire content of these United States patent documents is incorporated by reference herein.

Figure 8:
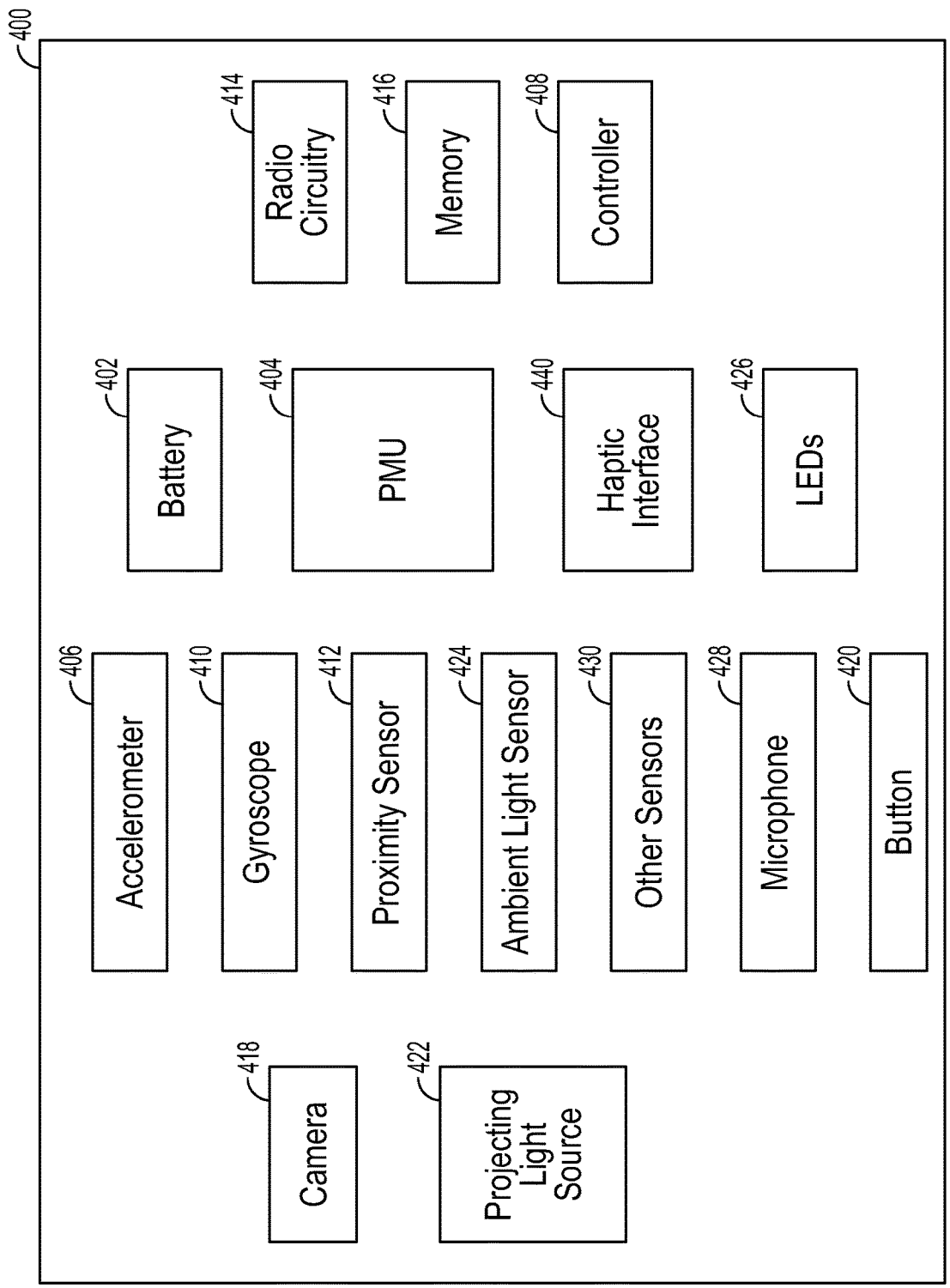
FIG. 8 is a block diagram representation of a gesture-based physical behavior detection system arranged in accordance with certain embodiments.

FIG. 8 is a block diagram representation of a gesture-based physical behavior detection system 400 arranged in accordance with certain embodiments. The system 400 is suitable for use with the system 100 shown FIG. 1. In certain embodiments, the system 400 is deployed as a wearable electronic device in the form factor of a bracelet or wristband that is worn around the wrist or arm of a user's dominant hand. The system 400 may optionally be implemented using a modular design, wherein individual modules include one or more subsets of the disclosed components and overall functionality. The user may choose to add specific modules based on personal preferences and requirements.

The system 400 includes a battery 402 and a power management unit (PMU) 404 to deliver power at the proper supply voltage levels to all electronic circuits and components. The PMU 404 may also include battery-recharging circuitry. The PMU 404 may also include hardware, such as switches, that allows power to specific electronics circuits and components to be cut off when not in use.

When there is no movement-based or gesture-based behavior event in progress, most circuitry and components in the system 400 are switched off to conserve power. Only circuitry and components that are required to detect or help predict the start of a behavior event of interest may remain enabled. For example, if no motion is being detected, all sensor circuits but an accelerometer 406 may be switched off and the accelerometer 406 may be put in a low-power wake-on-motion mode or in another lower power mode that consumes less power and uses less processing resources than its high performance active mode. A controller 408 of the system 400 may also be placed into a low-power mode to conserve power. When motion or a certain motion pattern is detected, the accelerometer 406 and/or the controller 408 may switch into a higher power mode and additional sensors such as, for example, a gyroscope 410 and/or a proximity sensor 412 may also be enabled. When a potential start of a movement-based or gesture-based event is detected, memory variables for storing event-specific parameters, such as gesture types, gesture duration, etc. can be initialized.

In another example, upon detection of user motion, the accelerometer 406 switches into a higher power mode, but other sensors remain switched off until the data from the accelerometer 406 indicates that the start of a behavior event has likely occurred. At that point in time, additional sensors such as the gyroscope 410 and the proximity sensor 412 may be enabled.

In another example, when there is no behavior event in progress, both the accelerometer 406 and gyroscope 410 are enabled but at least one of either the accelerometer 406 or the gyroscope 410 is placed in a lower power mode compared to their regular power mode. For example, the sampling rate may be reduced to conserve power. Similarly, the circuitry required to transfer data from the system 400 to a destination device may be placed in a lower power mode. For example, radio circuitry 414 could be disabled. Similarly, the circuitry required to transfer data from the system 400 may be placed in a lower power mode. For example, the radio circuitry 414 could be disabled until a possible or likely start of a behavior event has been determined. Alternatively, it may remain enabled but in a low power state to maintain the connection between the system 400 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the system 400 has been removed from the wrist or hand, detection that the system 400 is being charged, or the like. Metadata may be generated and collected by the system 400. Alternatively, metadata may be collected by another device that is external to the system 400 and is configured to directly or indirectly exchange information with the system 400. It is also possible that some metadata is generated and collected by the system 400, while other metadata is generated and collected by a device that is external to the system 400. In case some or all of the metadata is generated and collected external to the system 400, the system 400 may periodically or from time to time power up its radio circuitry 414 to retrieve metadata related information from another device.

In certain embodiments, some or all of the sensors may be turned on or placed in a higher power mode if certain metadata indicates that the occurrence of a particular behavior event, such as the user beginning to work, jog, or eat, is likely. Metadata used to make this determination may, among other things, include one or more of the following: time of the day; location; ambient light levels; proximity sensing; historical user behavior patterns. Some or all of the metadata may be collected by the system 400 or by an ancillary device that cooperates or communicates with the system 400, as mentioned above.

User status data used to track certain aspects of a user's behavior may be stored locally inside memory 416 of the system 400 and processed locally using the controller 408 of the system 400. User status data may also be transferred to the medication delivery system 102, the patient care application 110, and/or one or more of the database 114 mentioned above with reference to FIG. 1 (such that the user status data can be processed, analyzed, or otherwise utilized by the applications or components that receive the user status data). It is also possible that some of the processing and analysis are performed locally by the system 400, while further processing and analysis are performed by one or more other components of the system 100.

The detection of the start of a behavior event, such as the start of a work activity, may trigger the power up and/or activation of additional sensors and circuitry, such as a camera 418. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera 418 only gets powered up or activated upon explicit user intervention such as, for example, pushing and holding a button 420. Releasing the button 420 may turn off the camera 418 to conserve power.

When the camera 418 is powered up, a projecting light source 422 may also be enabled to provide visual feedback to the user about the area that is within view of the camera or to otherwise illuminate the field of view. Alternatively, the projecting light source 422 may only be activated sometime after the camera 418 has been activated. In certain cases, additional conditions may need to be met before the projecting light source 422 is activated. Such conditions may include: the determination that the projecting light source 422 is likely aiming in the direction of the object of interest; the determination that the system 400 is not moving excessively; or the like. In some embodiments, one or more light emitting diodes (LEDs) 426 may be used as the projecting light source 422.

Images may be tagged with additional information or metadata such as: camera focal information; proximity information from the proximity sensor 412; ambient light levels information from an ambient light sensor 424; timestamp information; etc. Such additional information or metadata may be used during the processing and analysis of the user status data.

The projecting light source 422 may also be used to communicate other information. As an example, an ancillary device may use inputs from one or more proximity sensors 412, process those inputs to determine if the camera 418 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 422 may also be used in combination with the ambient light sensor 424 to communicate to the user if the ambient light is insufficient or too strong for an adequate quality image capture. The projecting light source 422 may also be used to communicate information including, but not limited to, a low battery situation or a functional defect.

The projecting light source 422 may also be used to communicate dietary coaching information. As an example, the projecting light source 422 might, among other things, indicate if not enough or too much time has expired since a previous food intake event, or may communicate to the user how he/she is doing against specific dietary goals.

Signaling mechanisms to convey specific messages using one or more projecting light sources 422 may include, but are not limited to, one or more of the following: specific light intensities or light intensity patterns; specific light colors or light color patterns; specific spatial or temporal light patterns. Multiple mechanisms may also be combined to signal one specific message.

A microphone 428 may be used by the user to add specific or custom labels or messages to a detected event and/or image. In certain embodiments, audio captured by the microphone 428 can be processed to assist in the determination of whether the user is eating, drinking, commuting, exercising, working, or resting. Audio snippets may be processed by a voice recognition engine.

In certain embodiments, the accelerometer 406 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the system 400 may include or cooperate with any number of other sensors 430 as appropriate for the particular embodiment. For example, and without limitation, the system 400 may include or cooperate with any or all of the following: a heartrate monitor; a physiological characteristic or analyte sensor; a continuous glucose monitor; a GPS receiver; and any other sensor, monitor, or detector mentioned elsewhere herein. The system 400 obtains user status data from one or more of its sensors, detectors, and sources, wherein the user status data indicates a stressful activity of the user. The user status data can be analyzed and processed by the system 400 (and/or by one or more other components of the system 100) to determine whether the user's current behavior is consistent with normally expected behavior or activity. In certain embodiments, the system 400 and/or an ancillary system 106 or device determines the user's activity and related behavior primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the system 400 includes at least one haptic interface 440 that is suitably configured and operated to provide haptic feedback as an output. The at least one haptic interface 440 generates output(s) that can be experienced by the sense of touch by the user, e.g., mechanical force, vibration, movement, temperature changes, or the like. Haptic feedback generated by the at least one haptic interface 440 may represent or be associated with one or more of the following, without limitation: reminders; alerts; confirmations; notifications; messages; numerical values (such as measurements); status indicators; or any other type of output provided by the system 400.

In certain embodiments, the user status data (e.g., sensor data) is provided to a gesture recognizer unit or processor. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs (such as the output from one or more ancillary systems 106) to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processor. The event detector analyzes the incoming stream of gestures to determine if the start of an event of interest (e.g., eating a meal, going to bed, working out) has occurred, whether an event is ongoing, whether an event has ended, or the like. Although this description mentions meal detection, the gesture-based physical behavior detection system 400 may be suitably configured to monitor other types of physical behavior or activities. Such activities include, without limitation: reading; sleeping; smoking; getting dressed; driving; walking; commuting; working; exercising; turning down a bed; making a bed; brushing teeth; combing hair; talking on the phone; inhaling or injecting a medication; and activities related to hand hygiene or personal hygiene.

Figure 9:
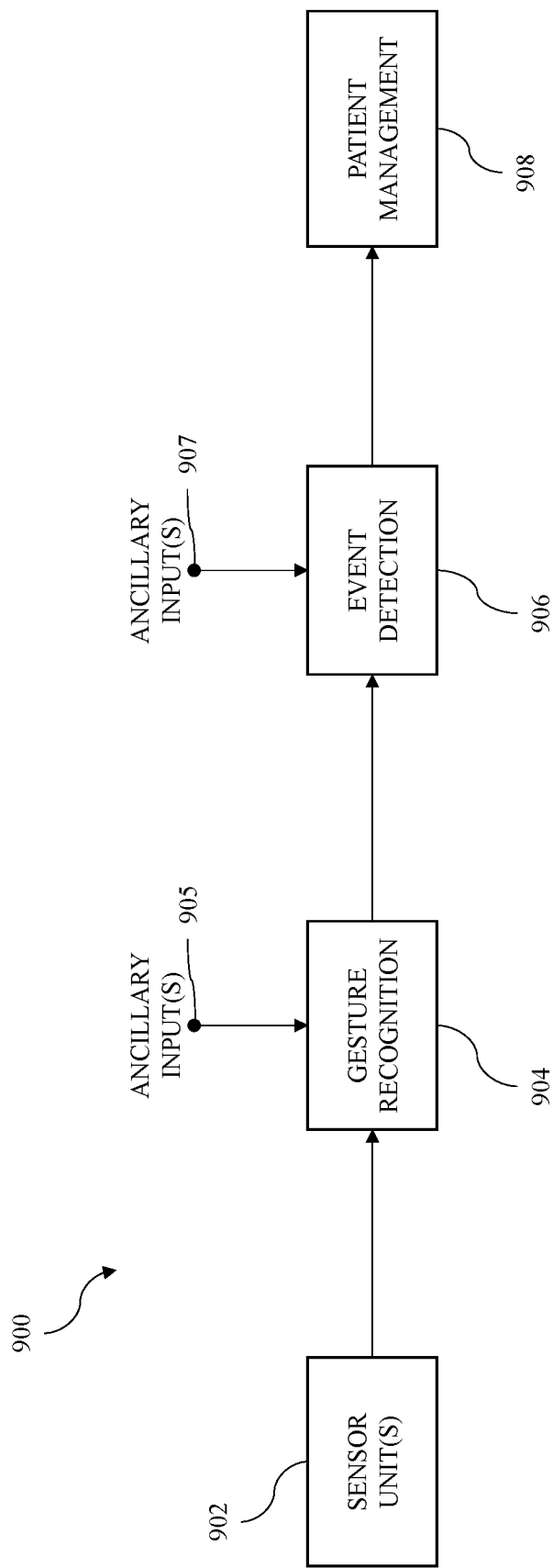
FIG. 9 is a block diagram representation of an embodiment of a gesture-informed patient management system 900 in accordance with certain embodiments.

FIG. 9 is a simplified block diagram representation of an embodiment of a gesture-informed patient management system 900. The depicted patient management system 90 includes, without limitation, one or more sensor units 902, a gesture recognition unit 904, an event detection unit 906, and a patient management unit 908.

The sensor unit(s) 902 generally represent the sensor(s) embedded in, integrated with, or otherwise associated with one or more portable or wearable devices associated with a patient, such as, for example, an activity tracker, a smart watch, a wristband, a ring, a mobile phone, or a portable electronic medical device (e.g., a continuous glucose monitoring device, an infusion device, an injection pen, and/or the like). For example, in one or more exemplary embodiments, the sensor unit(s) 902 include an accelerometer (e.g., accelerometer 406) and a gyroscope (e.g., gyroscope 412) associated with a smart watch. That said, it should be appreciated the patient management system 900 is not limited to any particular type, configuration, or number of sensor unit(s) 902, and in practice, the sensor unit(s) 902 may include one or more of the following sensing arrangements: accelerometers, gyroscopes, magnetometers, image sensors, cameras, optical sensors, proximity sensors, pressure sensors, odor sensors, gas sensors, Global Positioning Systems (GPS) receivers, microphones, galvanic skin response sensors, thermometers, ambient light sensors, UV sensors, electrodes for electromyographic ("EMG") potential detection, bio-impedance sensors, spectrometers, glucose sensors, heart rate sensors, pulse sensors, touchscreen or capacitive sensors. In this regard, the output of the sensor unit(s) 902 may include any sort of motion data, location data, physiological data (e.g., temperature, heart rate, pulse, galvanic skin response, blood or body chemistry, and/or the like), or other sensor data depending on the sensor type. The output of the sensor unit(s) 902 may be communicated to the gesture recognition unit 904 wirelessly or via wires, in analog or digital form, directly or indirectly (e.g., intermediated by gating and/or clocking circuits, analog-to-digital converters, and/or the like).

The gesture recognition unit 904 generally represents a software application or component of the patient management system 900 that receives the sensor data signals from the sensor unit(s) 902 and analyzes the received sensor data to detect or otherwise identify gestures performed by the patient based on the received sensor data. In this regard, a gesture generally represents a discrete set of one or more physical movements having associated spatial and/or temporal characteristics that are distinguishable from other gestures. For example, as described in United States Patent Publication Number 2020/0289373, the gesture recognition unit 904 may utilize machine learning or other artificial techniques to map different subsets of sensor data within a stream of received sensor data to different gesture features, which, in turn, are then analyzed to classify or otherwise resolve the different subsets of the sensor data and corresponding gesture features into a particular combination or sequence of gestures performed by the patient. In one or more embodiments, the gesture recognition unit 904 fuses or otherwise combines concurrent or otherwise temporally-associated accelerometer data and gyroscope data to obtain an orientation vector, with the concurrent or temporally-associated combinations of accelerometer data, gyroscope data, and fused orientation vectors being input to a feature generator, which, in turn, generates a corresponding stream of gesture features, which, in turn are input to the gesture recognition model which classifies or otherwise resolves the stream of gesture features into corresponding gestures. In exemplary embodiments, the gesture recognition unit 904 also associates or otherwise assigns a confidence metric to each gesture based on the gesture features. In this regard, for a given stream of sensor data received by the gesture recognition unit 904, the gesture recognition unit 904 outputs a corresponding stream of gestures and associated confidence levels.

In some embodiments, the gesture recognition unit 904 receives one or more ancillary inputs 905 which may influence the gesture detection or the confidence or probability assigned to detected gestures. For example, the ancillary input 905 may include operational contextual data, such as, the current time of day, the current day of the week, the current month of the year, the current location of the patient, and/or the like, along with other patient-specific data such as historical gesture data associated with the patient, a patient profile associated with the patient or other patient-specific personalization that may be utilized by the gesture recognition unit 904 to influence manner in which particular gesture features are mapped to a gesture for the particular patient. In this regard, statistical analysis of the historical gesture data and potentially other patient-specific data may be utilized to determine or otherwise assign probabilities of a specific gesture occurring based on the current operational context. It should be noted that there are any number of different types of ancillary input data (e.g., from at least one ancillary system 106 from FIG. 1) that may be correlative to the occurrence or non-occurrence of a particular gesture, and the subject matter described herein is not limited to any particular type or combination of ancillary inputs 905 that may be utilized by the gesture recognition unit 904.

In one or more embodiments, the executable code or programming instructions corresponding to the gesture recognition unit 904 is stored or otherwise maintained in a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by a processor or other processing system. For example, in one or more exemplary embodiments, the computer-executable programming instructions corresponding to the gesture recognition unit 904 are stored in a data storage element (e.g., memory 416) of a wearable electronic device including the sensor unit(s) 902, and, when read and executed by a processing system (e.g., controller 408) of the wearable electronic device, the instructions cause the wearable electronic device to generate the gesture recognition unit 904 at the wearable electronic device. In this regard, in some embodiments, the wearable electronic device may transmit or otherwise provide signals or data indicating a stream of detected gestures and associated confidence levels to another device for further processing and/or analysis. That said, in other embodiments, the gesture recognition unit 904 may be implemented at or on a patient's mobile phone or other portable electronic device (e.g., user device 108) that receives sensor data signals from the sensor unit(s) 902 via a wireless network, or be implemented at or on a cloud computing system or remote server that receives the sensor data signals from the sensor unit(s) 902 via the Internet, a cellular network, or the like.

Still referring to FIG. 9, the event detection unit 906 generally represents a software application or component of the patient management system 900 that receives the detected gestures and confidence levels from the from the gesture recognition unit 904 and analyzes the received gesture data to detect or otherwise identify events or activities performed by the patient based on the received gesture data. For example, as described in United States Patent Publication Number 2020/0289373, the event detection unit 906 may utilize machine learning or other artificial techniques to map a stream of detected gestures and associated confidence levels into a particular event or activity being performed by the patient based on the type of gestures detected, the sequence of detected gestures, the temporal relationship between gestures and/or the confidence metrics assigned to the detected gestures. In this manner, the event detection unit 906 may map lower-level gestures into a higher-level physical behavior while filtering or otherwise deemphasizing false positives or spurious gestures. Thus, for a given stream of detected gestures received by the event detection unit 906, the event detection unit 906 outputs an indication of a detected event or activity by the patient and an associated confidence or probability metric for the event. For example, for a sequence of detected food intake gestures may be mapped or otherwise recognized as a food intake event having a particular start time, pace, duration, and/or the like with an assigned level of confidence or probability influenced by the confidence associated with the detected food intake gestures and potentially other factors.

In a similar manner as described above for the gesture recognition unit 904, the event detection unit 906 may receive ancillary input 907 which may influence the event detection or the confidence or probability assigned to detected events. For example, the ancillary input 907 may include event log data associated with the patient that maintains data pertaining to historical events or activities by the patient (e.g., meals, exercise, sleep, boluses, glucose excursion events, and/or the like), with statistical analysis of the historical event log data and potentially other patient-specific data being utilized to determine or otherwise assign probabilities of a specific event occurring based on the current operational context. In this regard, if the patient habitually engages in meals at or around a certain time of day, food intake gestures occurring at that time of day consistent with the patient's historical behavior may be more likely to be mapped to a meal event or other food intake event, or the detected meal event or food intake event may be assigned a higher probability or confidence value based on the correlation and consistency with the patient's historical behavior. Again, it should be noted that there are any number of different types of ancillary input data that may be correlative to the occurrence or non-occurrence of a particular event, and the subject matter described herein is not limited to any particular type or combination of ancillary inputs 907 that may be utilized by the event detection unit 906.

In one or more embodiments, the executable code or programming instructions corresponding to the event detection unit 906 is stored or otherwise maintained in a data storage element or memory, including any sort of short or long term storage media or other non-transitory computer-readable medium, which is capable of storing programming instructions for execution by a processor or other processing system. For example, in one or more exemplary embodiments, the computer-executable programming instructions corresponding to the event detection unit 906 are stored in a data storage element (e.g., memory 416) of a wearable electronic device including the sensor unit(s) 902, and, when read and executed by a processing system (e.g., controller 408) of the wearable electronic device, the instructions cause the wearable electronic device to generate the event detection unit 906 at the wearable electronic device. In this regard, in some embodiments, the wearable electronic device may transmit or otherwise provide signals or data indicating a stream of detected events and associated confidence or probability levels to another device for further processing and/or analysis. That said, in other embodiments, the event detection unit 906 may be implemented at or on a patient's mobile phone or other portable electronic device (e.g., user device 108) or on a cloud computing system or remote server that receives gesture data signals from the gesture recognition unit 904 implemented at another device via a network.

Still referring to FIG. 9, the patient management unit 908 generally represents a software application or component of the patient management system 900 that receives the detected event data from the event detection unit 906 and automatically initiates or otherwise performs one or more actions with respect to management of the patient's physiological condition. In some embodiments, the patient management unit 908 is configurable to support one or more autonomous operating modes for an infusion device, a smart pen, or other fluid delivery device, where the patient management unit 908 calculates or otherwise determines dosage commands for operating an actuation arrangement to deliver fluid to the patient. For example, in a closed-loop operating mode, the patient management unit 908 may determine a dosage command based at least in part on a current glucose measurement value for the patient in a manner that is influenced by an event detected by the event detection unit 906. In some embodiments, the patient management unit 908 is configurable to generate or otherwise provide user notifications or alerts via a user interface element based at least in part on a detected event. In this regard, the patient management unit 908 may utilize patient-specific settings, preferences, or other notification criteria to automatically generate user notifications in a manner that is influenced by the detected event and potentially other factors (e.g., the patient's current or recent sensor glucose measurement values). For example, in one or more embodiments, for a patient on a MDI therapy regimen where the medication delivery system 102 includes a smart pen or other injection device, the patient management unit 908 may utilize patient-specific settings, preferences, or other notification criteria to automatically generate user notifications that indicate recommended bolus amounts, a recommended time (or window of time) for when a bolus should be delivered, and/or the like to assist the patient in administering an appropriate bolus that is responsive to a gestured event.

In one or more embodiments, the executable code or programming instructions corresponding to the patient management unit 908 is stored or otherwise maintained at one of the patient's associated devices (e.g., the patient's mobile phone, the patient's infusion device or other fluid delivery device, or the like) or at a cloud computing system or remote server. For example, the patient management unit 908 executing on the patient's phone may receive or otherwise obtain signals or data indicating detected gestures and/or events from the patient's smart watch or other wearable device, analyze the received data, and transmit or otherwise provide dosage commands or signals influenced by the detected gestured-based events to the patient's infusion device (e.g., via a wireless network) to automatically operate the infusion device to deliver insulin or another fluid or medicament to account for the detected event(s), or the patient management unit 908 may generate GUI displays or other user notifications influenced by the detected event(s) at the mobile device. That said, in other embodiments, when the patient management unit 908 is implemented at a remote server or other cloud computing system, the patient management unit 908 may transmit or otherwise provide dosage commands or signals to a device associated with the patient via a network. In yet other embodiments, the patient management unit 908 may be implemented at the patient's medical device and receive detected event data from the patient's mobile device, the patient's wearable device, or a remote server or other cloud computing system. In this regard, depending on the embodiment, the various units 904, 906, 908 may be distributed across one or more different devices 102, 104, 106, 108, 116 in a system 100 and the subject matter described herein is not limited to any particular implementation. For example, the event detection unit 906 and the patient management unit 908 may be implemented by the patient care application 110 at the user device 108 receiving the detected gesture data stream signals output by the gesture detection system 104 from the gesture detection system 104 via a wireless network.

Figure 10:
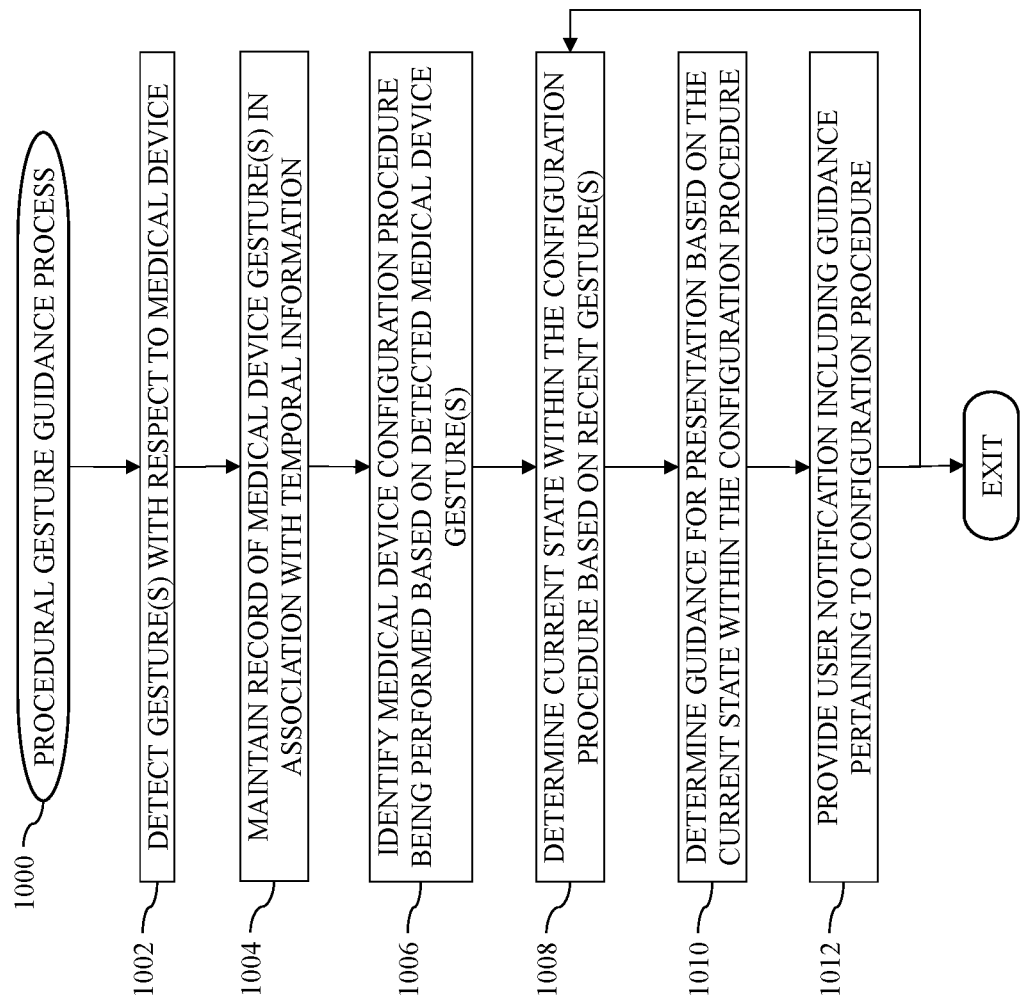
FIG. 10 is a flow diagram of an exemplary procedural gesture guidance process in accordance with one or more exemplary embodiments.

FIG. 10 depicts an exemplary procedural gesture guidance process 1000 suitable for implementation by a patient management system (e.g., patient management system 900) to provide guidance with respect to medical device configuration procedures involving one or more physical or mechanical tasks for installing, setting up, programming, operating or otherwise configuring the medical device for operation in a manner that is influenced by a detected gesture data stream substantially in real-time. In this regard, a configuration procedure may be defined by a sequence of physical or mechanical tasks that a patient or other user may need to perform as part of the configuration procedure relating to medical device operation, such as, for example, changing, rotating or replacing sensors or infusion sets, changing, replacing or refilling reservoirs, charging, changing or replacing batteries, taking blood glucose fingerstick reference measurements, delivering or injecting insulin (e.g., using an injection pen), and/or the like. Because the exact tasks (and sequence thereof) can be difficult to remember or follow for some individuals, the procedural gesture guidance process 1000 is capable of detecting where an individual is within a medical device configuration procedure and provide appropriate guidance or training materials to support completion of the procedure accurately and expeditiously. For example, one or more graphical user interface (GUI) displays may be provided on a patient's mobile device (e.g., by a patient care application 110 at a user device 108) to provide step-by-step guidance for completing the configuration procedure. The guidance may also incorporate or otherwise support chatbot functionality or other features that allow a patient to obtain answers to frequently asked questions or otherwise interface with training materials to improve the user experience. In this regard, when the patient's gesture data indicates the patient is attempting to change a sensor, infusion set, pump reservoir, or the like, a patient care application 110 or patient management unit 908 may automatically generate GUI displays or other user notifications that facilitate the patient efficiently and expeditiously completing the relevant medical device configuration procedure while avoiding mistakes.

The various tasks performed in connection with the procedural gesture guidance process 1000 may be performed by hardware, firmware, software executed by processing circuitry, or any combination thereof. For illustrative purposes, the following description refers to elements mentioned above in connection with FIGS. 1-9. It should be appreciated that the procedural gesture guidance process 1000 may include any number of additional or alternative tasks, the tasks need not be performed in the illustrated order and/or the tasks may be performed concurrently, and/or the procedural gesture guidance process 1000 may be incorporated into a more comprehensive procedure or process having additional functionality not described in detail herein. Moreover, one or more of the tasks shown and described in the context of FIG. 10 could be omitted from a practical embodiment of the procedural gesture guidance process 1000 as long as the intended overall functionality remains intact.

The procedural gesture guidance process 1000 initializes or otherwise begins by identifying, recognizing, or otherwise detecting gestures with respect to a patient's medical device (task 1002). For example, as described above, the gesture recognition unit 904 may be trained to classify, resolve, or otherwise map different subsets of sensor data within a stream of sensor data received from the sensor unit 902 to a particular gesture (or combination or sequence thereof) using machine learning. In this regard, based on the sensor data stream from the sensor unit 902, the gesture recognition unit 904 may detect a user performing a particular type of gesture with respect to a sensor, infusion set, infusion device, reservoir, or other medical device or component for configuring, setting up, installing, replacing, or otherwise performing a procedure with respect to that medical device or component. The gesture recognition unit 904 transmits, outputs, or otherwise provides indicia of the detected procedural medical device gestures to the event detection unit 906.

In exemplary embodiments, the procedural gesture guidance process 1000 records, stores or otherwise maintains indicia of the detected procedural medical device gestures in association with timestamps or other temporal information associated with the underlying subsets of sensor data corresponding to the procedural gestures (task 1004). In this regard, the start time, the end time, the duration, and other temporal characteristics or attributes associated with a particular gesture with respect to a medical device may be stored or otherwise maintained by the event detection unit 906, the patient management unit 908 and/or another element of a patient management system 900 (e.g., in memory 204).

In some embodiments, the temporal information associated with detected procedural medical device gestures may be transmitted or otherwise uploaded to a database 114 for a population-level retrospective analysis by a remote server or other cloud computing system (e.g., data processing system 116). In this regard, temporal information associated with procedural medical device gestures across different patients or users may be utilized to calculate or otherwise determine one or more metrics for scoring or otherwise characterizing procedural medical device gestures. For example, the temporal data associated with procedural gestures may be analyzed to determine the average or estimated amount of time required to perform a particular procedural medical device gesture and score or rate the relative difficulty of the procedural gesture based on the average time required.

The recorded procedural medical device gesture data may also be utilized to identify the rate or frequency at which a particular gesture is required to be repeated or performed erroneously, which may also be utilized to score or rate the relative difficulty of the procedural gesture, independently or in concert with the amount of time required for the gesture. In this regard, qualitative or quantitative difficulty or complexity scores may be assigned to different procedural gestures, which, in turn, may be utilized to influence the guidance provided for those gestures, as described in greater detail below.

It should be noted that the different procedural gestures may also be scored for difficulty or complexity on a patient-specific basis, for example, based on the patient's procedural gesture data relative to the population procedural gesture data. For example, if a particular patient typically completes a particular task in less time than the average amount of time for that task across the entire population of patients or users, the qualitative or quantitative difficulty or complexity scores assigned to that gesture or task for that patient may be less than what would be assigned for other patients or users that require an above average amount of time.

The procedural gesture guidance process 1000 identifies or otherwise determines the configuration procedure the patient or other user is attempting to perform with respect to the medical device and the current state of the patient or user within that medical device procedure based on the detected gestures (tasks 1006, 1008). In a similar manner as described above, the event detection unit 906 may be trained to classify, resolve, or otherwise map a combination or sequence of gestures with respect to one or more medical devices within the detected gesture data stream provided by the gesture recognition unit 904 to a particular configuration procedure being performed with respect to a patient's medical device. For example, machine learning or other artificial techniques may be utilized to develop one or more models capable of mapping a sequence of detected procedural medical device gestures into a particular medical device configuration procedure being performed by the patient based on the type of procedural medical device gestures detected, the sequence of detected procedural gestures, the temporal relationship between procedural gestures and/or the confidence metrics assigned to the detected procedural gestures. In this manner, the event detection unit 906 may map lower-level procedural medical device gestures into a higher-level medical device configuration procedure being performed.

For example, each defined physical or mechanical task that a patient or other user may need to perform as part of a defined sequence for a configuration procedure relating to medical device operation may entail one or more distinct gestures with respect to the medical device that correspond to that particular physical or mechanical task within the defined configuration procedure sequence of tasks. Thus, when a stream of detected gestures received by the event detection unit 906 matches or otherwise corresponds to a combination or sequence of procedural gestures that correspond to the defined sequence of tasks of a particular medical device configuration procedure, the event detection unit 906 transmits, outputs or otherwise provides an indication of a detected medical device configuration procedure being performed by the patient. Additionally, based on the most recently detected medical gesture with respect to the combination or sequence of gestures associated with the detected medical device procedure, the event detection unit 906 may also transmit, output or otherwise provide an indicia of the current state within the medical device configuration procedure in concert with identification of the medical device procedure being performed. In this regard, based on the preceding combination or sequence of procedural gestures detected by the gesture recognition unit 904, the event detection unit 906 may identify the tasks of the configuration procedure sequence that have already been performed by the patient and identify the next sequential task following the most recently completed task in the sequence as the current task awaiting performance by the patient.

Based on the current state within the detected medical device configuration procedure being performed, the procedural gesture guidance process 1000 determines or otherwise identifies guidance pertaining to the detected medical device configuration procedure for presentation and generates or otherwise provides a user notification including the determined guidance (tasks 1010, 1012). In this manner, in response to the event detection unit 906 detecting a medical device configuration procedure being performed by a patient and identifying the current patient state within that configuration procedure, the patient management unit 908 may automatically generate a GUI display at the patient's user device 108 (e.g., via patient care application 110) that includes guidance specific to the current patient state within the medical device configuration procedure substantially in real-time without requiring any interaction by the patient with respect to the user device 108 and/or patient care application 110. For example, the guidance may include text, verbal, graphics, images, videos, or any sort of audio-visual content that facilitates completion of the medical device configuration procedure (e.g., by providing indication of the next mechanical or physical task to be performed in the medical device configuration procedure sequence) or enhances execution of the medical device configuration procedure (e.g., by providing indication of optional tasks for advanced features or functionality). In this regard, in various embodiments, the guidance may be personalized based on the patient's gesture data or other historical data associated with the patient. For example, based on the temporal characteristics associated with the patient's procedural medical device gestures or the temporal relationships between successive procedural gestures within the medical device configuration procedure, the patient management unit 908 may calculate or otherwise determine values for one or more experiential metrics that rate, score, or otherwise assess the patient's relative level of skill with respect to the medical device configuration procedure (or a particular task thereof) and provide guidance influenced by the patient's score or skill level. Additionally, or alternatively, based on the patient's historical data, the patient management unit 908 may rate, score, or otherwise assess the patient's relative level of experience with respect to use of the medical device and provide guidance influenced by the patient's experience level.

In one or more embodiments, the guidance content is influenced by any qualitative or quantitative difficulty or complexity scores assigned to the current patient state within the medical device configuration procedure. For example, if the next mechanical or physical task to be performed in the medical device configuration procedure sequence has a relatively higher rate or frequency of error or repetition and/or a relatively higher average amount of time required associated therewith, the guidance may include a video (or a hypertext link to a video) that includes a more detailed illustration or explanation for how to perform the task, while an image or textual explanation may be provided for a task with a relatively lower rate or frequency of error or repetition and/or a relatively lower average amount of time required associated therewith.

In one or more exemplary embodiments, the tasks 1008, 1010, and 1012 may repeat throughout the duration of time the medical device configuration procedure is being performed to dynamically update the guidance substantially in real-time to reflect the current state within the configuration procedure as the patient or user advances through the medical device configuration procedure. For example, when the detected gesture data stream output by the gesture recognition unit 904 indicates the patient has performed a physical or mechanical task corresponding to the previously displayed guidance at the patient care application 110 on the user device 108, the event detection unit 906 dynamically updates the indication of the current patient state within the medical device configuration procedure and the patient management unit 908 dynamically updates the GUI display presented by the patient care application 110 on the user device 108 substantially in real-time to reflect completion of that task and include guidance pertaining to the next physical or mechanical task to be performed by the patient within the medical device configuration procedure. Thus, the patient or other user can receive step-by-step guidance or feedback via the patient care application 110 on the user device 108 while performing a maintenance, setup, installation, or other configuration procedure with respect to a medical device (e.g., a medication delivery system 102, an analyte sensor 112, an ancillary system 106, or the like) without requiring the patient to divert his or her hands from the medical device to interact with the user device 108 to update the guidance.

For example, in response to output from the sensor unit 902 indicative of gestures being performed with respect to a patient's medical device, the gesture recognition unit 904 and the event detection unit 906 may be cooperatively configured to detect the particular configuration procedure that the patient is performing (or attempting to perform) with respect to the medical device, and based on the particular combination and sequence of detected gestures that the patient has already performed with respect to the patient's medical device, determine the patient's current state within the defined sequence of tasks for the configuration procedure. The patient's current state within the defined sequence of tasks for the configuration procedure may be utilized by the patient management unit 908 to identify or otherwise determine current task or step of the configuration procedure that the patient's is currently attempting to perform following any tasks already completed by the patient, and then determine and present guidance content for performing the current task. In this regard, the amount or other characteristics of the guidance content may be influenced by the value for one or more difficulty metrics associated with the current task and/or the value for one or more experiential metrics associated with the patient. For example, when the value for a difficulty metric associated with the current task is above a threshold value and/or the value for an experiential metric associated with the patient is below a threshold value, the patient management unit 908 may determine that a greater amount of guidance content should be presented, that more detailed guidance content should be presented and/or that richer or more engaging guidance content should be prevented to better assist the patient with the current task. Conversely, when the difficulty metric is below a threshold value and/or the value for an experiential metric associated with the patient is above a threshold value, the patient management unit 908 may determine that a lesser amount of more simplified guidance content should be presented since the patient is likely to require less assistance with the current task. Moreover, in some scenarios, the patient management unit 908 may determine the guidance content should pertain to an advanced or optional feature associated with the current task or the configuration procedure to facilitate better utilization of the medical device features or functionality when the patient is unlikely to require assistance.

Thereafter, in response to subsequent output from the sensor unit 902 indicative of gestures corresponding to performance of the current task of the configuration procedure, the gesture recognition unit 904 and/or the event detection unit 906 may be cooperatively configured to detect the performance of the task and provide a corresponding indicia to the patient management unit 908, which, in turn, dynamically updates the presented guidance information to reflect the completion of the task of the configuration procedure the patient was previously on. In this regard, the patient management unit 908 may identify or otherwise determine subsequent task or step of the configuration procedure that followed the recently completed task is now the current task, and then similarly determine and present guidance content for performing that task based on the difficulty metric(s) associated with the task and/or the experiential metric(s) associated with the patient for that task. Thus, the amount, detail, and other characteristics of the presented guidance content may dynamically vary throughout performance of the configuration procedure as the patient progresses between more difficult and less difficult tasks.

It should be appreciated the procedural gesture guidance process 1000 may be utilized to provide improved training and adherence to proper medical device operation or configuration, and improve familiarity with different device features, actions or capabilities that could otherwise be underutilized. In this regard, the procedural gesture guidance process 1000 may provide an improved onboarding experience with step-by-step guidance that may be tailored to individual users or individual mechanical or physical tasks within a procedure based on the relative complexity or difficulty associated with those tasks. For example, children or adolescents may utilize different gesture movements associated with handling system components while also having differing levels of comprehending how to execute different tasks. Accordingly, the gesture recognition unit 904 and/or the event detection unit 906 may be trained using data sets derived from particular age groups or other classifications of patients or users, thereby allowing the gesture recognition unit 904 and/or the event detection unit 906 to better identify procedural gestures and corresponding medical procedures being performed for similar patients or users belonging to those age groups. The age-stratified data sets may also be utilized to relative complexity or difficulty associated with different tasks across a particular age group, which may be utilized to better tailor guidance for patients or users belonging to that age group. For example, training videos or other guidance can be made more effective by focusing on the more difficult tasks in greater detail, while training or guidance may be simplified for less difficult tasks to reduce the amount of time or attention required and improve the user experience. Improving a patient's user experience and ability to understand and execute medical device procedures may also improve adherence to those procedures (e.g., by replacing or changing sensors or infusion sets at a recommended replacement interval).

An individual's procedural medical device gesture data may also be utilized to score or otherwise assess an individual's skill, experience, or familiarity with respect to particular features, functionality, or device capabilities, which, in turn, may be utilized to push additional training materials or guidance to a particular individual, provide remote training for that particular individual, or otherwise improve troubleshooting or managing complaints by that particular individual. For example, a patient's historical procedural medical device gesture data may be analyzed to determine one or more experiential metrics that score or grade how the patient changes an insulin cartridge (e.g., how effectively or efficiently the patient performs connecting, rewinding and/or priming of the cartridge based on time required, repetition frequency, etc.), how the patient inserts an interstitial glucose sensor (e.g., based on the patient's insertion angle data derived from the gesture data, the time required and/or repetition frequency for pressing and/or taping the sensor, etc.), how the patient operates a medical device (e.g., based on the amount of time required to mute alerts, request or administer a bolus, make changes to device settings, etc.), and/or the like.

After determining a personalized score for performing the configuration procedure (or a task thereof) based on the patient's historical procedural gesture data, the patient management unit 908 generates or otherwise provides guidance information in a manner that is influenced by the patient's personalized score. For example, when the patient's personalized score for the configuration procedure (or the current task thereof) is greater than a threshold value indicating a more experienced or advanced user, the patient management unit 908 may determine, generate, select or otherwise obtain guidance content for an advanced feature associated with the configuration procedure (or the current task thereof). Conversely, when the patient's personalized score for the configuration procedure (or the current task thereof) is less than a threshold value indicating a less experienced or beginner user, the patient management unit 908 may determine, generate, select or otherwise obtain more detailed guidance content to assist completion of the current task.

In addition to providing real-time guidance tailored to an individual patient's skill, experience and/or familiarity, the scoring or other characterization of a patient's historical procedural medical device gesture data may be utilized to provide additional supplemental guidance to patients in a patient-specific manner. For example, a remote server or other cloud-based processing system 114 may be configured to periodically analyze a patient's historical procedural medical device gesture data in the database 116 and automatically push or otherwise provide guidance to the patient's user device 108 and/or the patient care application 110 regarding specific device features that the patient may be experiencing difficulty with or underutilizing, such as, for example, sending an e-mail or other electronic message with information pertaining to best practices for specific device features, replaying or repeating certain information about device features in the patient care application 110, prompting or automatically scheduling a call or other meeting with support personnel to discuss specific device features, and/or the like.

The patient's historical procedural medical device gesture data may also be used in the context of insertion site usage monitoring and related insertion site rotation guidance or other insertion site notifications. For example, the gesture recognition unit 904 and the event detection unit 906 may be trained or otherwise cooperatively configured to detect insertion events or site change events based on the patient's gestures with respect to a medical device. In response to the event detection unit 906 detecting an insertion site event, the patient management unit 908 may automatically generate guidance pertaining to the insertion site event, such as, for example, outputting instructions or training material pertaining to the detected insertion site event or providing reminders to reorder supplies (and/or automatically directing the patient care application 110 to a website for reordering supplies). The patient management unit 908 may also utilize the detected insertion site event gesture data to automatically update or adjust reminders for future insertion site changes. The detected insertion site event gesture data may also be analyzed to collect statistics pertaining to the patient's insertion site usage or otherwise derive metrics for the patient's insertion site usage, which, in turn, may be utilized to automatically and dynamically generate insertion site recommendations in a patient-specific manner to achieve better insertion site utilization. Some examples of insertion site algorithms or applications that may utilize the detected insertion site event gesture data as a potential input are described in U.S. Pat. Nos. 10,201,657, 10,272,201 and U.S. patent application Ser. No. 17/086,147.

Detection of procedural medical device gestures and related events may also be utilized to facilitate automatic logging of patient behavior, thereby reducing patient burdens and improving user experience. For example, patients on a manual therapy regimen may generally be required to manually log injection events, sensor changes, and the like. In this regard, automatically recording or logging the procedural medical device gesture events in concert with other gestured events (e.g., meal events or other food intake events, exercise events, and/or the like) provides an improved record of the patient's behavior that facilitates a patient's healthcare provider analyzing the patient's behavior and optimizing the patient's therapy in a patient-specific manner. For example, in response to the event detection unit 906 detecting an injection event (e.g., based on the procedural medical device gestures of filling a syringe and manipulating an injection pen), the patient management unit 908 may automatically generate a GUI display within the patient care application 110 at the patient's user device 108 substantially in real-time that prompts the patient to input the amount of insulin being injected for recordation or logging in association with the gestured injection event (e.g., by uploading the amount of insulin and the time associated with the injection event to a remote processing system 116 for analysis and/or storage in a remote database 114). Accordingly, a more accurate diary or log of insulin doses may be obtained, which, in turn improves health care provider decisions on therapy recommendations. Additionally, or alternatively, the log of insulin doses may also be analyzed by an automatic therapy advisor algorithm (e.g., at a cloud-based processing system 116) in concert with the patient's glucose measurement data (e.g., obtained via analyte sensor 106) to automatically determine optimal therapy guidance that may be transmitted or otherwise provided to the user device 108 and generated or otherwise displayed by the patient care application 110 in response to an injection event.

Figure 11:
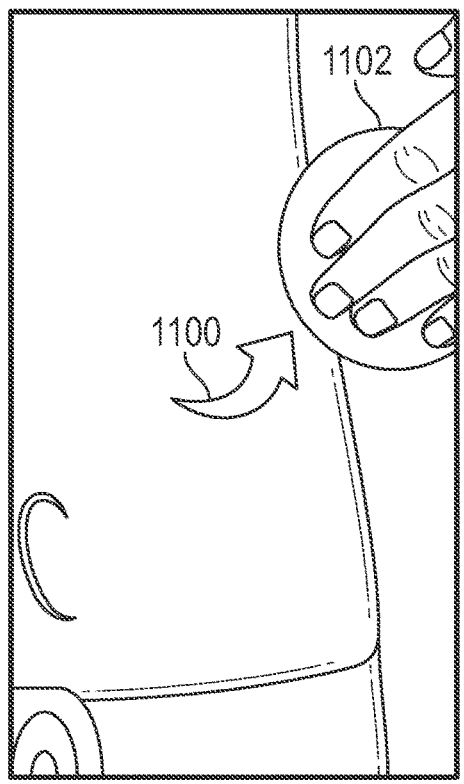
FIG. 11 depicts a graphical representation of a procedural gesture suitable for detection in connection with an exemplary embodiment of the procedural gesture guidance process of FIG. 10.
Figure 12:
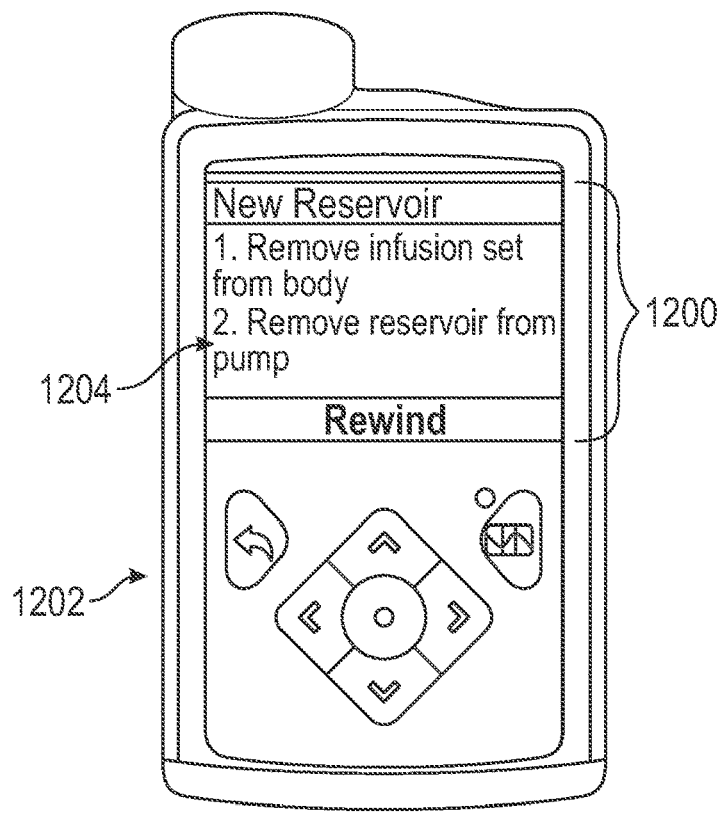
FIG. 12 depicts an exemplary graphical user interface display suitable for presentation in connection with an exemplary embodiment of the procedural gesture guidance process of FIG. 10 responsive to the procedural gesture depicted in FIG. 11 in accordance with one embodiment.

Referring now to FIGS. 11-12, the procedural gesture guidance process 1000 of FIG. 12 may be configured to provide a configuration procedure GUI display 1200 on a display of an electronic device associated with a patient, such as an infusion device 1202, in response to detecting a procedural gesture 1100 corresponding to the patient detaching or otherwise removing an infusion set 1102 from the patient's body. In response to detecting the gesture 1100 based on movement of the patient's hand or wrist, the procedural gesture guidance process 1000 determines the patient is attempting to replace a reservoir of the infusion device 1202. Based on the patient's current state within the reservoir replacement configuration procedure, the procedural gesture guidance process 1000 generates or otherwise provides the configuration procedure GUI display 1200 that includes graphical indicia 1204 of the next task of the reservoir replacement configuration procedure to be performed by the patient, thereby reminding or otherwise informing the patient of what the patient needs to do next to effectuate the reservoir replacement. In some embodiments, the graphical indicia 1204 may be realized as a hyperlink or other selectable GUI element which the patient may select or otherwise activate to cause the procedural gesture guidance process 1000 to generate or otherwise provide more detail explanatory text for how to perform the next task or a video or other illustration or imagery of how to perform the next task (e.g., a video of a reservoir cap or fitting being unscrewed from the infusion device). In this manner, the procedural gesture guidance process 1000 facilitates successful and expeditious performance of the detected configuration procedure by providing guidance information relative to the tasks yet to be performed by the patient.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of assisting operation of a personal medical device configured to be carried by or secured to a user and that regulates delivery of fluid to the user, using a sensing arrangement capable of detecting physical movement by the user, the method comprising:
   detecting, by a control system associated with the personal medical device, a configuration procedure being performed by the user on the personal medical device to configure the personal medical device, the detecting in response to output of the sensing arrangement indicative of one or more gestures with respect to the personal medical device by the user;
   accessing, by the control system, a pre-defined sequence of user tasks forming the configuration procedure to configure the personal medical device;
   determining, by the control system, a current task awaiting performance by the user in the pre-defined sequence of user tasks, the determining based at least in part on the one or more gestures by the user with respect to the personal medical device relative to a sequence of gestures corresponding to the pre-defined sequence of user tasks for the configuration procedure; and
   providing, by the control system, a graphical user interface on a display comprising guidance information for the current task to be performed by the user within the pre-defined sequence of user tasks forming the configuration procedure.

2. The method of claim 1, further comprising determining guidance content for performing the current task of the pre-defined sequence of user tasks based at least in part on a difficulty metric associated with the current task, wherein the guidance information comprises the guidance content.

3. The method of claim 2, further comprising:
   detecting performance of the current task in response to a subsequent output of the sensing arrangement indicative of one or more subsequent gestures with respect to the personal medical device by the user; and
   in response to the performance of the current task, dynamically updating the graphical user interface on the display to provide second guidance content for performing a subsequent task of the pre-defined sequence of user tasks following the current task.

4. The method of claim 3, further comprising determining the second guidance content for performing the subsequent task based at least in part on a second difficulty metric associated with the subsequent task, wherein a second amount of the second guidance content varies from a first amount of the guidance content in a manner corresponding to a relationship between the second difficulty metric and the difficulty metric.

5. The method of claim 1, further comprising determining a personalized score for performing the configuration procedure based on historical procedural gesture data associated with the user, wherein the guidance information is influenced by the personalized score associated with the user.

6. The method of claim 5, further comprising determining guidance content for an advanced feature associated with the configuration procedure for the personal medical device when the personalized score indicates an experienced user, wherein the guidance information comprises the guidance content for the advanced feature.

7. The method of claim 5, wherein the guidance information comprises detailed guidance content for performing the current task of the pre-defined sequence of user tasks when the personalized score indicates an inexperienced user.

8. At least one non-transitory computer readable medium having stored thereon program code instructions that are configurable to cause at least one processor to perform a method comprising:
   detecting a configuration procedure being performed by a user with respect to a personal medical device configured to be carried by or secured to the user and that regulates delivery of fluid to the user, the detecting in response to output of a sensing arrangement indicative of one or more gestures with respect to the personal medical device by the user, wherein the sensing arrangement is capable of detecting physical movement by the user;
   accessing a pre-defined sequence of user tasks forming the configuration procedure to configure the personal medical device;
   determining a current task awaiting performance by the user in the pre-defined sequence of user tasks, the determining based at least in part on the one or more gestures by the user with respect to the personal medical device relative to a sequence of gestures corresponding to the pre-defined sequence of user tasks for the configuration procedure; and
   providing a graphical user interface on a display comprising guidance information for the current task to be performed by the user within the pre-defined sequence of user tasks forming the configuration procedure.

9. The at least one non-transitory computer readable medium of claim 8, wherein the method further comprises determining guidance content for performing the current task of the pre-defined sequence of user tasks based at least in part on a difficulty metric associated with the current task, wherein the guidance information comprises the guidance content.

10. The at least one non-transitory computer readable medium of claim 9, wherein the method further comprises:
    detecting performance of the current task in response to a subsequent output of the sensing arrangement indicative of one or more subsequent gestures with respect to the personal medical device by the user; and
    in response to the performance of the current task, dynamically updating the graphical user interface on the display to provide second guidance content for performing a subsequent task of the pre-defined sequence of user tasks following the current task.

11. The at least one non-transitory computer readable medium of claim 10, wherein the method further comprises determining the second guidance content for performing the subsequent task based at least in part on a second difficulty metric associated with the subsequent task, wherein a second amount of the second guidance content varies from a first amount of the guidance content in a manner corresponding to a relationship between the second difficulty metric and the difficulty metric.

12. The at least one non-transitory computer readable medium of claim 8, wherein the method further comprises determining a personalized score for performing the configuration procedure based on historical procedural gesture data associated with the user, wherein the guidance information is influenced by the personalized score associated with the user.

13. The at least one non-transitory computer readable medium of claim 12, wherein the method further comprises determining guidance content for an advanced feature associated with the configuration procedure for the personal medical device when the personalized score indicates an experienced user, wherein the guidance information comprises the guidance content for the advanced feature.

14. The at least one non-transitory computer readable medium of claim 12, wherein the guidance information comprises detailed guidance content for performing the current task of the pre-defined sequence of user tasks when the personalized score indicates an inexperienced user.

15. A system comprising:
    a personal medical device configured to be carried by or secured to a patient and that regulates delivery of fluid to the patient;
    a gesture detection system configured to generate gesture data for the patient, and configured to communicate the gesture data; and
    at least one controller that controls operation of the personal medical device, the at least one controller configured to:
      detect a configuration procedure being performed by the patient on the personal medical device to configure the personal medical device, the detecting in response to the gesture data indicative of one or more procedural gestures with respect to the personal medical device by the patient;
      access a pre-defined sequence of user tasks forming the configuration procedure to configure the personal medical device;
      determine a current task awaiting performance by the patient in the pre-defined sequence of user tasks, the determining based at least in part on the one or more procedural gestures by the patient with respect to the personal medical device relative to a sequence of gestures corresponding to the pre-defined sequence of user tasks for the configuration procedure; and provide a graphical user interface on a display comprising guidance information for the current task to be performed by the patient within the pre-defined sequence of user tasks forming the configuration procedure.

16. The system of claim 15, wherein the at least one controller is configured to determine guidance content for performing the current task of the pre-defined sequence of user tasks based at least in part on a difficulty metric associated with the current task, wherein the guidance information comprises the guidance content.

17. The system of claim 16, wherein the at least one controller is configured to:

detect performance of the current task in response to one or more subsequent gestures with respect to the personal medical device by the patient; and in response to the performance of the current task, dynamically update the graphical user interface on the display to provide second guidance content for performing a subsequent task of the pre-defined sequence of user tasks following the current task.

18. The system of claim 17, wherein the at least one controller is configured to determine the second guidance content for performing the subsequent task based at least in part on a second difficulty metric associated with the subsequent task, wherein a second amount of the second guidance content varies from a first amount of the guidance content in a manner corresponding to a relationship between the second difficulty metric and the difficulty metric.

19. The system of claim 15, wherein the at least one controller is configured to determine a personalized score for performing the configuration procedure based on historical gesture data associated with the patient, wherein the guidance information is influenced by the personalized score associated with the patient.

* * * * *